(12) United States Patent
Branton et al.

(10) Patent No.: US 6,730,662 B1
(45) Date of Patent: May 4, 2004

(54) ADENOVIRUS E4 PROTEINS FOR INDUCING CELL DEATH

(75) Inventors: Philip E. Branton, Lambert (CA); Gordon C. Shore, Montreal (CA); Jose G. Teodoro, Worchester, MA (US); Richard C. Marcelius, Montreal (CA); Josee N. Lavoie, Montreal (CA)

(73) Assignee: McGill University, Montreal (CA)

( * ) Notice: Subject to any disclaimer, the term of this patent is extended or adjusted under 35 U.S.C. 154(b) by 0 days.

(21) Appl. No.: 09/214,478

(22) PCT Filed: Jul. 3, 1997

(86) PCT No.: PCT/IB97/01041
§ 371 (c)(1),
(2), (4) Date: Jun. 7, 1999

(87) PCT Pub. No.: WO98/01563
PCT Pub. Date: Jan. 15, 1998

Related U.S. Application Data

(60) Provisional application No. 60/028,740, filed on Oct. 22, 1996, now abandoned, and provisional application No. 60/021,273, filed on Jul. 5, 1996, now abandoned.

(51) Int. Cl.[7] .......................... A01N 43/04; A01N 63/00; C12N 15/00; C12N 15/63; C07G 17/00
(52) U.S. Cl. ...................... 514/44; 435/320.1; 435/267; 435/455; 536/23.1; 424/93.2
(58) Field of Search .................. 514/44; 536/23.1, 536/23.7; 435/320.1, 455, 267; 424/93.2

(56) References Cited

U.S. PATENT DOCUMENTS 5,994,106 A * 11/1999 Kovesdi et al. ............ 435/91.4
5,998,205 A * 12/1999 Hallenbeck et al. ........ 435/325
6,100,086 A *  8/2000 Kaplan et al. ............ 435/320.1

FOREIGN PATENT DOCUMENTS

WO    WO 96/13596    5/1996
WO    WO 96/14061    5/1996
WO    WO 96/22378    7/1996
WO    WO 96/39530   12/1996

OTHER PUBLICATIONS

Chroboczek et al., GenEmbl Accession No. M73260, Apr. 1996.*
Herisse et al., PIR_63 Accession No. A03805, 1982.*
Chrodoczek et al., ACC: M73260, 1996, Gene Embl.*
Swinkles et al., The yeast Kluyveromyces lactic as an efficient host for heterologous gene expression, 1993, vol. 64, p. 187–201.*
Rudinger et al., Characteristics of the amino acids as compeonents of a peptide hormone sequence, Biological Council, Jun. 1976, pp. 1–7.*
Ohgi et al., Expression of RNase Rh from Rhizopus niveus in Yeast and Characterization of the Secreted Proteins, J. Biochem., vol. 109, 1991, pp. 776–785.*

Eck et al., Gene–Based Therapy, Goodman & Gilman's The Pharmacological Basis of Therapeutics, Ninthe edition, 1996, pp. 77–101.*
Verma et al., Gene therapy promises,problems and prospects, Nature, vol. 389, Sep. 1997, pp. 239–242.*
Crystal, Transfer of Genes to Humans: Early Lessons and Obstacles to Success, Science 1995, Vol 270, pp. 404–410.*
Deonarain, Ligand–targeted receptors–medicated vectors for gene delivery, Ashley Publications Ltd., 1998, pp. 53–69.*
Miller et al., Targeted vectors for gene therpy, The FASEB Journal, Feb. 1995, vol. 9, pp. 190–199.*
Bridge et al., "Redundant control of adenovirus late gene expression by early region 4," *J. Virol.* 63:631–638 (1989).
Bridge et al., "Adenovirus early region 4 and viral DNA synthesis," *J. Virol.* 193:794–801 (1993).
Corbeil et al., "Functional importance of complex formation between the retinoblastoma tumor suppressor family and adenovirus E1A proteins as determined by mutational analysis of E1A conserved region 2," *J. Virol.*, 68:6697–6709 (1994).
Herisse et al., "Nucleotide sequence of adenovirus 2 DNA fragment encoding for the carboxylic region of the fiber protein and the entire E4 region," *Nucleic Acid Res.* 9:4023–4042 (1981).
Ketner et al., "Complementation of adenovirus E4 mutants by transient expression of E4 cDNA and deletion plasmids," *Nucleic Acid Res.* 17:3037–3048 (1989).
Kleinberger and Shenk "Adenovirus E4orf4 protein binds to protein phosphatase 2A and the complex down regulates E1A–enhanced junB transcription," *J. Virol.* 67:7556–7560 (1993).
Lowe et al., "Abrogation of oncongene–associated apoptosis allows transformation of p53–deficient cells," *Proc. Nat'l Acad. Sci.* USA 91:2026–2030 (1994).
Marcellius et al., Adenovirus type 5 early region 4 is responsible for E1A–induced p53–independent apoptosis, *J. Virol.* 70:6207–6215 (1996).
McLorie et al., Individuals adenovirus E1B proteins induce transformation independently but by additive pathways, *J. Viol.* 72:1467–1471 (1991).
Nguyen et al., "Role of membrane anchor domain of Bcl–2 in suppression of apoptosis caused by E1B–defective adenovirus," *J. Biol. Chem.* 269:16521–16524 (1994).

(List continued on next page.)

Primary Examiner—Shin-Lin Chen
(74) Attorney, Agent, or Firm—Clark & Elbing, LLP; Kristina Bieker-Brady, Ph.D.

(57) ABSTRACT

The invention features E4orf4-encoding nucleic acids, pharmaceutical compositions and expression vectors containing the same, and methods for their use. E4orf4-encoding nucleic acids include (i) nucleic acids capable of hybridizing at high stringency to the complement of the nucleic acid encoding Ad2E4orf4, and (ii) nucleic acids having 50% or greater nucleotide sequence identity to the nucleotide sequence of Ad2E4orf4, so long as the nucleic acids encode a polypeptide capable of inducing apoptosis.

10 Claims, 19 Drawing Sheets

OTHER PUBLICATIONS

Subramanian et al., "p53–independent apoptotic and necrotic cell deaths induced by adenovirus infection: suppression by E1B 19K and Bcl–2 proteins," *Cell Growth Differ.* 6:131–137 (1995).

Teodoro et al., "Phosphorylation at the carboxy terminus of the 55–kilodalton adenovirus type 5 E1B protein regulates transforming activity," *J. Virol.* 68: 776–786 (1994).

Teodoro et al., "Adenovirus E1A proteins induce apoptosis by both p53–dependent and p53–independent mechanisms," *Oncogene* 11:467–474 (1995).

* cited by examiner

| VIRUS MUTANT | DESCRIPTION |
|---|---|
| wt Ad5 | wt E1A (12S & 13S mRNAs), wt E1B. In some cases $dl$ 309 which has a partial deletion of E3 was used |
| 12S / E1B- | 12S E1A mRNA only, no E1B expression |
| 13S / E1B- | 13S E1A mRNA only, no E1B expression |
| E1B / 55K- | wtE1A (12S & 13S mRNAs), no E1B 55K expression, wt E1B 19K |
| E1B / 19K- | wtE1A (12S & 13S mRNAs), no E1B 19K expression, wt E1B 55K |
| $dl$ 1101 / E1B- | 12S/13S E1A mRNAs, E1A mutation as in Fig. 1A, no E1B expression |
| $dl$ 1104 / E1B- | 12S/13S E1A mRNAs, E1A mutation as in Fig. 1A, no E1B expression |
| $dl$ 1107 / E1B- | 12S/13S E1A mRNAs, E1A mutation as in Fig. 1A, no E1B expression |
| $dl$ 1108 / E1B- | 12S/13S E1A mRNAs, E1A mutation as in Fig. 1A, no E1B expression |
| $dl$ 1143 / 08/ E1B- | 12S/13S E1A mRNAs, E1A mutation as in Fig. 1A, no E1B expression |
| AR1- / E1B- | 12S/13S E1A mRNAs, E1A mutation as in Fig. 1A, no E1B expression |
| AR2- / E1B- | 12S/13S E1A mRNAs, E1A mutation as in Fig. 1A, no E1B expression |
| AR1- / AR2- / E1B- | 12S/13S E1A mRNAs, E1A mutation as in Fig. 1A, no E1B expression |
| AD147VL / E1B- | 13S E1A only, E1A point mutation in CR3, no E1B expression |
| AD171CS / E1B- | 13S E1A only, E1A point mutation in CR3, no E1B expression |
| AD185SG / E1B- | 13S E1A only, E1A point mutation in CR3, no E1B expression |
| $dl$ 1019 | wt E1A, E1B, E2 and E3, no E4 expression, in Ad2 |
| AdLacZ | no E1A or E1B expression, wt E2, E3 and E4 |
| Ad5$dl$70-8 | no E1A, E1B or E3 expression, wt E2 and E4 |
| AdRSVβ-gal.11 | no E1A, E1B or E4 expression, wt E2 and E3 |

Fig. 1B

Ad5 E4orf6

```
         10        20        30        40
atgactacgtccggcgttccatttggcatgacactacgac  40
caacacgatctcggttgtctcggcgcactccgtacagtag  80
ggatcgtctacctcctttgagacagaaacccgcgctacc  120
atactggaggatcatccgctgctgcccgaatgtaacactt  160
tgacaatgcacaacgtgagttacgtgcgaggtcttccctg  200

210       220       230       240
cagtgtgggatttacgctgattcaggaatgggttgttccc  240
tgggatatggttctaacgcgggaggagcttgtaatcctga  280
ggaagtgtatgcacgtgtgcctgtgttgtgccaacattga  320
tatcatgacgagcatgatgatccatggttacgagtcctgg  360
gctctccactgtcattgttccagtcccggttccctgcagt  400

410       420       430       440
gtatagccggcgggcaggttttggccagctggtttaggat  440
ggtggtggatggcgccatgtttaatcagaggtttatatgg  480
taccgggaggtggtgaattacaacatgccaaaagaggtaa  520
tgtttatgtccagcgtgtttatgaggggtcgccacttaat  560
ctacctgcgcttgtggtatgatggccacgtgggttctgtg  600

610       620       630       640
gtccccgccatgagctttggatacagcgccttgcactgtg  640
ggatttgaacaatattgtggtgctgtgctgcagttactg  680
tgctgatttaagtgagatcagggtgcgctgctgtgcccgg  720
aggacaaggcgccttatgctgcgggcggtgcgaatcatcg  760
ctgaggagaccactgccatgttgtattcctgcaggacgga  800

810       820       830       840
gcggcggcggcagcagtttattcgcgcgctgctgcagcac  840
caccgccctatcctgatgcacgattatgactctacccca  880
tgtag  885
```

```
         10        20        30        40
MTTSGVPFGMTLRPTRSRLSRRTPYSRDRLPPFETETRAT  40
ILEDHPLLPECNTLTMHNVSYVRGLPCSVGFTLIQEWVVP  80
WDMVLTREELVILRKCMHVCLCCANIDIMTSMMIHGYESW  120
ALHCHCSSPGSLQCIAGGQVLASWFRMVVDGAMFNQRFIW  160
YREVVNYNMPKEVMFMSSYFMRGRHLIYLRLWYDGHVGSV  200

210       220       230       240
VPAMSFGYSALHCGILNNIVVLCCSYCADLSEIRVRCCAR  240
RTRRLMLRAVRIIAEETTAMLYSCRTERRRQQFIRALLQH  280
HRPILMHDYDSTPM. 295
```

Fig. 15

Ad5 E4orf4

```
          10        20        30        40
atggttcttccagctcttcccgctcctcccgtgtgtgact  40
cgcagaacgaatgtgtaggttggctgggtgtggcttattc  80
tgcggtggtggatgttatcagggcagcggcgcatgaagga 120
gtttacatagaacccgaagccagggggcgcctggatgctt 160
tgagagagtggatatactacaactactacacagagcgatc 200

210       220       230       240
taagcggcgagaccggagacgcagatctgtttgtcacgcc 240
cgcacctggttttgcttcaggaaatatgactacgtccggc 280
gttccatttggcatgacactacgaccaacacgatctcggt 320
tgtctcggcgcactccgtacagtag 345
```

```
          10        20        30        40
MVLPALPAPPVCDSQNECVGWLGVAYSAVVDVIRAAAHEG  40
VYIEPEARGRLDALREWIYYNYYTERSKRRDRRRRSVCHA  80
RTWFCFRKYDYVRRSIWHDTTTNTISVVSAHSVQ.      115
```

Fig.16

ADENOVIRUS E4 PROTEINS FOR INDUCING CELL DEATH

CROSS-REFERENCE TO RELATED APPLICATIONS

This application is a 371 of PCT/IB97/01041 (filed Jul. 3, 1997), and claims benefit from U.S. Provisional Application Nos. 60/021,273 (filed Jul. 5, 1996) and 60/028,740 (filed. Oct. 22, 1996), each of which is now abandoned.

BACKGROUND OF THE INVENTION (a) Field of the Invention

The invention relates to a pharmaceutical agent(s) to induce cell death for use in treating conditions which involve inappropriate cell survival.

(b) Description of Prior Art

Replication of human adenoviruses in terminally differentiated epithelial cells requires an efficient mechanism to induce cellular DNA synthesis. This induction permits replication of viral DNA and production of progeny virus. Human adenoviruses infect and kill epithelial cells very efficiently. Cell death occurs by apoptosis and virus spread occurs through endocytosis by surrounding cells.

Products of early region 1A (E1A) of the adenovirus genome induce cell DNA synthesis and are largely responsible for cell transformation by adenoviruses. E1A produces two major mRNAs of 13S and 12S which encode proteins of 289 and 243 residues (289R and 243R, respectively) that are identical except for the lack in 243R of a central 46-amino acid sequence, termed conserved region 3 or CR3, as schematically depicted in FIG. 1A. Two additional regions present in the common sequence encoded by exon 1 of both E1A mRNAs are also conserved in all human adenovirus serotypes and have been termed CR1 and CR2. E1A products induce DNA synthesis through ,complex formation between CR2 and CR1 and the retinoblastoma tumor suppressor pRB and related p107 and p130 proteins, or between the amino terminus and CR1 and the transcriptional modulator p300 and possibly related proteins (Corbeil, H. B. et al., 1994, J. Virol. 68: 6697–6709). E1A-289R also activates expression of the early viral transcription units E2, E3, and E4, and certain cellular genes at least in part through interactions with transcription factors and basal transcription machinery requiring CR3 (Teodoro, J. G. et al., 1995, Oncogene 11: 467–474). In addition to CR3, transactivation of the E4 promoter has also been shown to rely to some degree on two regions encoded by the second exon of 13S mRNA, termed auxiliary regions 1 and 2, or AR1 and AR2. Production of stably transformed cells requires early region 1B (E1B) which encodes polypeptides of 19 and 55 kDa that are individually capable of cooperating with E1A via separate but additive pathways (McLorie, W. et al., 1991, J. Gen. Virol. 72: 1467–1471).

Considerable evidence indicates that a major function of E1B proteins in lytic infection and cell transformation is to suppress cytotoxic effects and apoptosis induced by expression of E1A. Without E1B, the toxicity of E1A products results in the death of E1A-transformed cells and a reduction in the yield of progeny due to the early demise of productively infected cells. E1A proteins can cause apoptosis by a process mediated by the tumor suppressor p53, which controls growth arrest and programmed cell death pathways (Teodoro, J. G. et al., 1995, Oncogene 11: 467–474). Expression of E1A products results in the elevation of p53 levels. The 55 kDa E1B protein binds to p53 and blocks both p53-mediated activation of gene expression and apoptosis (Teodoro, J. G. et al., 1994, J. Virol. 68: 776–786). The 19 kDa E1B protein appears to suppress apoptosis by a mechanism that is functionally analogous to that of the cellular proto-oncogene product Bcl-2 (Nguyen, M. et al., 1994, J. Biol. Chem. 269: 16521–16524). Cells infected with adenovirus mutants which fail to express the 19 kDa protein display enhanced cytotoxicity and extensive degradation of both cellular and viral DNA into nucleosome sized fragments (McLorie, W. et al., supra; Teodoro, J. G. et al., 1995, Oncogene 11: 467–474). At later times, even in the presence of E1B proteins, infected cells suffer apoptotic death and viral progeny spread to neighboring cells through endocytosis of cell fragments. In addition to the induction of DNA synthesis and cell transformation, the large 289-residue (289R) E1A protein also transactivates expression of all early viral genes, including early regions 1A, 1B, 2, 3 and 4 (reviewed in Teodoro, J. G. et al., 1995, Oncogene 11: 467–474).

It would be highly desirable to be provided with a pharmaceutical agent for induction of apoptosis when such induction is useful in the treatment of human diseases which involve inappropriate cell survival.

SUMMARY OF THE INVENTION

In accordance with the present invention, we have used a genetic approach to identify the role of individual E4 proteins in the induction of p53-independent apoptosis. Our results indicate the E4 death proteins, E4orf4 or E4orf6, are responsible for induction of p53-apoptosis in transformed, but not untransformed, cells. Thus, E4orf4 and E4orf6 are both powerful inducers of p53-independent cell death. This discovery has significant ramifications for both apoptosis-inducing therapeutics and drug screens.

In a first aspect, the invention provides a method of increasing apoptosis in a cell by administering to the cell an apoptosis inducing amount of an E4orf6 polypeptide or an apoptotic fragment thereof. In a preferred embodiment of this aspect, the apoptosis is p53-independent.

In a second aspect, the invention provides a method of increasing apoptosis in a mammal which includes providing a transgene encoding an E4orf6 polypeptide or an apoptotic fragment thereof to a cell of the mammal. The transgene is positioned for expression in the cell, and preferably encodes E4orf6.

In a third aspect, the invention provides a method of increasing apoptosis in a cell which includes administering to the cell a compound which increases E4orf6 biological activity. In various preferred embodiments, the compound is E4orf6 mRNA, or increases the stability of E4orf6.

In a preferred embodiment of the first and third aspects of the invention, the cell is in a mammal, preferably a human.

In a fourth aspect, the invention provides a method of increasing apoptosis in a cell by administering to the cell an apoptosis inducing amount of an E4orf4 polypeptide or an apoptotic fragment thereof. In a preferred embodiment of this aspect, the apoptosis is p53-independent.

In a fifth aspect, the invention provides a method of increasing apoptosis in a mammal which includes providing a transgene encoding an E4orf4 polypeptide or an apoptotic fragment thereof to a cell of the mammal. The transgene is positioned for expression in the cell, and preferably encodes E4orf4.

In a sixth aspect, the invention provides a method of increasing apoptosis in a cell which includes administering to the cell a compound which increases E4orf4 biological activity. In various preferred embodiments, the compound is E4orf4 mRNA, or increases the stability of E4orf4.

In a preferred embodiment of the fourth and sixth aspects of the invention, the cell is in a mammal, preferably a human.

In a seventh aspect, the invention provides a method of increasing apoptosis in a cell by administering to the cell an apoptosis inducing amount of a composition which includes an E4orf6 polypeptide or an apoptotic fragment thereof and an E4orf4 polypeptide or an apoptotic fragment thereof. In a preferred embodiment of this aspect, the apoptosis is p53-independent.

In an eighth aspect, the invention provides a method of increasing apoptosis in a mammal which includes providing a first transgene encoding an E4orf6 polypeptide or fragment thereof and a second transgene encoding an E4orf4 polypeptide or fragment thereof to a cell of the mammal. The first and second transgenes are positioned for expression in the cell and, preferably, encode E4orf6 and E4orf6, respectively.

In a ninth aspect, the invention provides a method of increasing apoptosis in a cell which includes administering to the cell a composition which includes a first compound which increases E4orf6 biological activity and a second compound which increases E4orf4 biological activity. In various preferred embodiments, the first compound is E4orf6 mRNA, or increases stability of E4orf6, and the second compound is E4orf4 mRNA or increases stability of E4orf4.

In a preferred embodiment of the seventh and ninth aspects of the invention, the cell is in a mammal, preferably a human.

In preferred embodiments of all the above aspects of the invention, the cell is in a mammal diagnosed as having a disease involving insufficient apoptosis. Preferably, the disease is cancer.

In a tenth aspect, the invention features a pharmaceutical composition which includes substantially pure nucleic acid encoding an E4orf6 polypeptide and a pharmaceutically acceptable carrier. In one embodiment of this aspect, the nucleic acid encodes E4orf6 having a conservative amino acid substitution relative to the E4orf6 sequence of FIG. 15 (SEQ ID NO.: 2).

In an eleventh aspect, the invention features a pharmaceutical composition which includes nucleic acid encoding an apoptotic fragment of E4orf6.

In a preferred embodiment of the tenth and eleventh aspects of the invention, the nucleic acid is in a viral vector. In another embodiment, the nucleic acid is operably linked to regulatory sequences for expression of the polypeptide and the regulatory sequences include a promoter. In another embodiment, the promoter is a constitutive promoter, is inducible by one or more external agents, or is cell-type specific.

In a twelfth aspect, the invention features a pharmaceutical composition which includes a nucleic acid having the sequence of FIG. 15 (SEQ ID NO.: 1), or degenerate variants thereof, and encoding the amino acid sequence of FIG. 15 (SEQ ID NO.: 2).

In a thirteenth aspect, the invention features a pharmaceutical composition which includes nucleic acid having about 50% or greater nucleotide sequence identity to the DNA sequence of FIG. 15 (SEQ ID NO.: 1), where the nucleic acid encodes a polypeptide with E4orf6 apoptotic biological activity. In one embodiment of this aspect of the invention, the nucleotide sequence identity is 75% or greater to the DNA sequence of FIG. 15 (SEQ ID NO.: 1).

In a fourteen aspect, the invention features a pharmaceutical composition which includes a DNA sequence substantially identical to the DNA sequence of FIG. 15 (SEQ ID NO.: 1).

In a fifteenth aspect, the invention features pharmaceutical composition which includes substantially pure mammalian E4orf6 polypeptide, or apoptotic fragment thereof. In one embodiment of this aspect, the polypopetide includes an amino acid sequence substantially identical to the amino acid sequence shown in FIG. 15 (SEQ ID NO.: 2). In another embodiment, the polypeptide has a conservative amino acid substitution relative to the E4orf6 sequence of FIG. 15 (SEQ ID NO.: 2).

In a sixteenth aspect, the invention features a pharmaceutical composition which includes a substantially pure polypeptide fragment of E4orf6.

In a seventeenth aspect, the invention features a pharmaceutical composition which includes substantially pure nucleic acid encoding an E4orf4 polypeptide and a pharmaceutically acceptable carrier. In one embodiment of this aspect, the nucleic acid encodes E4orf4 having a conservative amino acid substitution relative to the E4orf4 sequence of FIG. 16 (SEQ ID NO.: 4).

In an eighteenth aspect, the invention features a pharmaceutical composition which includes nucleic acid encoding an apoptotic fragment of E4orf4.

In a preferred embodiment of the seventeenth and eighteenth aspects of the invention, the nucleic acid is in a viral vector. In another embodiment, the nucleic acid is operably linked to regulatory sequences for expression of the polypeptide and the regulatory sequences include a promoter. In another embodiment, the promoter is a constitutive promoter, is inducible by one or more external agents, or is cell-type specific.

In a nineteenth aspect, the invention features a pharmaceutical composition which includes a nucleic acid having the sequence of FIG. 16 (SEQ ID NO.: 3), or degenerate variants thereof, and encoding the amino acid sequence of FIG. 16 (SEQ ID NO.: 4).

In a twentieth aspect, the invention features a pharmaceutical composition which includes nucleic acid having about 50% or greater nucleotide sequence identity to the DNA sequence of FIG. 16 (SEQ ID NO.: 3), where the nucleic acid encodes a polypeptide with E4orf4 apoptotic biological activity. In one embodiment of this aspect of the invention, the nucleotide sequence identity is 75% or greater to the DNA sequence of FIG. 16 (SEQ ID NO.: 3).

In a twenty-first aspect, the invention features a pharmaceutical composition which includes a DNA sequence substantially identical to the DNA sequence of FIG. 16 (SEQ ID NO.: 3).

In a twenty-second aspect, the invention features pharmaceutical composition which includes substantially pure mammalian E4orf4 polypeptide, or apoptotic fragment thereof. In one embodiment of this aspect, the polypopetide includes an amino acid sequence substantially identical to the amino acid sequence shown in FIG. 16 (SEQ ID NO.: 4). In another embodiment, the polypeptide has a conservative amino acid substitution relative to the E4orf4 sequence of FIG. 16 (SEQ ID NO.: 4).

In a twenty-third aspect, the invention features a pharmaceutical composition which includes a substantially pure polypeptide fragment of E4orf4.

In the twenty-fourth and twenty-fifth aspects, the invention features methods for identifying a compound as an E4orf6 analog or an E4orf4 analog which includes first providing a cell expressing the adenovirus E1A-289R protein while not expressing any E4 proteins. The cell is then contacted with a candidate compound and cell viability is determined, where death in the cell indicates a compound that is an E4orf6 or an E4orf4 analog.

In one embodiment of the twenty-fourth and twenty-fifth aspects of the invention, the cell is selected from the group consisting of: 1A.A3, 1A.A6, and 1A.A12 cells. In other preferred embodiments, the viability is measured with Trypan Blues™, a DNA fragmentation assay, an Annexin V binding assay, or Propidium Iodide, or a combination thereof. In yet another embodiment, the cell is infected with a mutant adenovirus incapable of expressing any E4 proteins.

In a twenty-sixth aspect, the invention features a method for identifying a compound as an E4orf4 analog which includes first providing a cell expressing protein phosphatase 2A. The cell is then contacted with the compound the activity of the protein phosphatase 2A in the cell is measured, where an increase in the activity relative to a cell not contacted indicates a compound that is an E4orf4 analog.

In a twenty-seventh aspect, the invention features a pharmaceutical agent for induction of apoptosis for the treatment of human diseases which involve inappropriate cell survival, which includes E4orf6, an analog, or a biologically active fragment thereof.

In a twenty-eighth aspect, the invention features a pharmaceutical composition for the treatment of human diseases which involve inappropriate cell survival, which includes a therapeutical amount of E4orf6, an analog, or a biologically active fragment thereof in association with a pharmaceutical carrier.

In a twenty-ninth aspect, the invention features a pharmaceutical composition for the treatment of human diseases which involve inappropriate cell survival, which includes a therapeutic amount of a compound which induces apoptosis or other cytotoxic effects analogous to E4orf6 biological activity in association with a pharmaceutical carrier.

In a thirtieth aspect, the invention features a pharmaceutical agent for induction of apoptosis for the treatment of human diseases which involve inappropriate cell survival, which includes E4orf4, an analog, or a biologically active fragment thereof.

In a thirty-first aspect, the invention features a pharmaceutical composition for the treatment of human diseases which involve inappropriate cell survival, which includes a therapeutic amount of E4orf4, an analog, or a biologically active fragment thereof in association with a pharmaceutical carrier.

In a thirty-second aspect, the invention features a pharmaceutical composition for the treatment of human diseases which involve inappropriate cell survival, which includes a therapeutic amount of a compound which induces protein phosphates 2a in association with a pharmaceutical carrier. In one embodiment of this aspect, the compound is an agonist of E4orf4. In another embodiment, the compound mimics E4orf4 activity.

In a thirty-third aspect, the invention features a pharmaceutical composition for the treatment of human diseases which involve inappropriate cell survival, which includes a therapeutic amount of a compound which induces apoptosis or other cytotoxic effects analogous to E4orf4 biological activity in association with a pharmaceutical carrier.

In a thirty-fourth aspect, the invention features a pharmaceutical agent for induction of apoptosis for the treatment of human diseases which involve inappropriate cell survival, which includes E4orf6, an analog, or a biologically active fragment thereof; and E4orf4, an analog, or a biologically active fragment thereof.

In a thirty-fifth aspect, the invention features a pharmaceutical composition for the treatment of human diseases which involve inappropriate cell survival, which includes a therapeutical amount of E4orf6, an analog, or a biologically active fragment thereof; and E4orf4, an analog, or a biologically active fragment thereof in association with a pharmaceutical carrier.

In a thirty-sixth aspect, the invention features a pharmaceutical composition for the treatment of human diseases which involve inappropriate cell survival, which includes a therapeutic amount of a compound which induces apoptosis or other cytotoxic effects analogous to biological activities of the E4 death proteins in association with a pharmaceutical carrier.

Compositions of the invention include, but are not limited to, E4orf4 protein, E4orf6 protein, combinations thereof, nucleic acids encoding the E4orf4 and E4orf6 polypeptides, analogs, mimetics, and any agonist therapeutic agents identified using any of the methods disclosed herein. The compositions may be administered with a pharmaceutically-acceptable diluent, carrier, or excipient, in unit dosage form. Conventional pharmaceutical practice may be employed to provide suitable formulations or compositions to administer such compositions to patients.

In accordance with the present invention, the expression "diseases which involve inappropriate cell survival" includes, without limitation, diseases caused by HIV, herpes and/or other viral infections, Alzheimer's disease, cancer, arthritis, and lupus.

In accordance with the present invention, "E4 death proteins" include products encoded by DNA capable of hybridizing at high stringency conditions to nucleic acids encoding E4orf6 (SEQ ID NO.: 1) and E4orf4 (SEQ ID NO.: 3), provided in FIGS. 15 and 16 respectively, and which also have E4orf6 and/or E4orf4 biological activity. Products are encoded by DNA that is at least 500 nucleotides in length, preferably, less than 200 nucleotides in length, more preferably, less than 150 nucleotides in length, and most preferably, less than 100 nucleotides in length. It will be understood that E4orf6 and E4orf4 proteins and nucleic acids of the invention may be obtained from any adenovirus strain having the E4orf6 or E4orf4 open reading frames, as defined as an open reading frame which is at least 20%, preferably 50%, more preferably 75%, and most preferably 90% identical to the E4orf6 (SEQ ID NO. 2) and E4orf4 (SEQ ID NO.: 4) open reading frames, respectively, provided herein.

In accordance with the present invention, "E4orf6 proteins" and "E4orf6 polypeptides" include products encoded by DNA capable of hybridizing at high stringency conditions to nucleic acids encoding E4orf6 (SEQ ID NO.: 1) provided in FIG. 15, and which also have E4orf6 biological activity. Products are encoded by DNA that is at least 500 nucleotides in length, preferably, less than 200 nucleotides in length, more preferably, less than 150 nucleotides in length, and most preferably, less than 100 nucleotides in length. It will be understood that E4orf6 proteins and nucleic acids of the invention may be obtained from any adenovirus strain having the E4orf6 open reading frame, as defined as an open reading frame which is at least 20%, preferably 50%, more preferably 75%, and most preferably 90% identical to the E4orf6 open reading frame (SEQ ID NO.: 2) provided herein.

In accordance with the present invention, "E4orf4 proteins" and "E4orf4 polypeptides" include products encoded by DNA capable of hybridizing at high stringency conditions to nucleic acids encoding E4orf4 (SEQ ID NO.: 3), provided in FIG. 16, and which also have E4orf4 biological activity. Products are encoded by DNA that is at least 500 nucleotides in length, preferably, less than 200 nucleotides in length, more preferably, less than 150 nucleotides in length, and most preferably, less than 100 nucleotides in length. It will be understood that E4orf4 proteins and nucleic acids of the invention may be obtained from any adenovirus strain having the E4orf4 open reading frame, as defined as an open reading frame which is at least 20%, preferably 50%, more preferably 75%, and most preferably 90% identical to the E4orf4 open reading frame (SEQ ID NO.: 4) provided herein.

In accordance with the present invention, the expression "high stringency conditions" means conditions that allow DNA hybridization to nucleic acids encoding E4orf6 (SEQ ID NO.: 1) or E4orf4 (SEQ ID NO.: 3) at high stringency (e.g., hybridizing in 2×SSC at 40° C. with a DNA probe length of at least 40 nucleotides). For other definitions of high stringency conditions, see Ausubel, F. et al., 1994, *Current Protocols in Molecular Biology*, John Wiley & Sons, New York, 6.3.1–6.3.6, hereby incorporated by reference.

In accordance with the present invention, the expression "E4orf6 biological activity" means the ability to induce in E1A-289R expressing cells an increased cell death that is 25%, more preferably 40%, and most preferably 60% greater than the cell death observed in E1A-289R expressing cells not expressing E4orf6, an apoptotic fragment, or analog thereof. E4orf6 biological activity is determined using one of the assays provided herein, preferably the luciferase death assay using 1A.A3, 1A.A6, or 1A.A12 cells. It will be understood that E1A-289R may be from any adenovirus strain.

In accordance with the present invention, the expression "E4orf4 biological activity" means the ability to induce in E1A-289R expressing cells an increased cell death that is 50%, more preferably 75%, and most preferably 90% greater than the cell death observed in E1A-289R expressing cells not expressing E4orf4, an apoptotic fragment, or analog thereof. E4orf6 biological activity is determined using one of the assays provided herein, preferably the luciferase death assay using 1A.A3, 1A.A6, or 1A.A12 cells. It will be understood that E1A-289R may be from any adenovirus strain.

In accordance with the present invention, the expression "promoter" means a minimal sequence sufficient to direct transcription. Also included in the invention are those promoter elements which are sufficient to render promoter-dependent gene expression controllable for cell type-specific, tissue-specific or inducible by external signals or agents; such elements may be located in the 5' or 3' regions of the native gene.

In accordance with the present invention, the expression "degenerate variant" means nucleic acid sequences or combinations thereof selected from all possible coding sequences for E4orf6 and E4orf4, or polypeptide fragments thereof, based upon the universal genetic code.

In accordance with the present invention, the expression "operably linked" means that a gene and one or more regulatory sequences are connected in such a way as to permit gene expression when the appropriate molecules (e.g., transcriptional activator proteins) are bound to the regulatory sequences.

In accordance with the present invention, the expression "positioned for expression" means that the nucleic acid is positioned adjacent to a nucleic acid sequence which directs transcription and translation of the sequence (i.e., facilitates the production of, e.g., an E4orf4 polypeptide, a recombinant protein or a RNA molecule).

In accordance with the present invention, the expression "substantially identical" means a polypeptide or nucleic acid exhibiting at least 50%, preferably 75%, more preferably 90%, and most preferably 95% identity to a reference amino acid or nucleic acid sequence. For polypeptides, the length of comparison sequences will generally be at least 16 amino acids, preferably at least 20 amino acids, more preferably at least 25 amino acids, and most preferably at least 35 amino acids. For nucleic acids, the length of comparison sequences will generally be at least 50 nucleotides, preferably at least 70 nucleotides, more preferably at least 90 nucleotides, and most preferably at least 120 nucleotides.

Sequence identity is typically measured using sequence analysis software with the default parameters specified therein (e.g., Sequence Analysis Software Package of the Genetics Computer Group, University of Wisconsin Biotechnology Center, 1710 University Avenue, Madison, Wis. 53705). This software program matches similar sequences by assigning degrees of homology to various substitutions, deletions, and other modifications. Conservative substitutions typically include substitutions within the following groups: glycine, alanine, valine, isoleucine, leucine; aspartic acid, glutamic acid, asparagine, glutamine; serine, threonine; lysine, arginine; and phenylalanine, tyrosine.

By "transformed cell" is meant a cell which is immortalized. For example, a transformed cell will divide and give rise to two daughter cells of the same differentiation status as the parent cell. A transformed cell may be a cell into which (or into an ancestor of which) has been introduced an exogenous gene or gene product (e.g., an oncogene) which allows immortalization of that cell. A transformed cell may also arise from a genomic mutation in an endogenous gene, giving rise to a mutated gene product, or dysregulation of a endogenous gene product. Transformed cells are differentiated from stem cells in that transformed cells have an alteration affecting normal gene expression and/or regulation. Exemplary transformed cells include cancerous cells such as those found in solid and liquid tumors.

In accordance with the present invention, the expression "transgene" means any piece of DNA which is inserted by artifice into a cell, and becomes part of the genome of the organism which develops from that cell. Such a transgene may include a gene which is partly or entirely heterologous (i.e., foreign) to the transgenic organism, or may represent a gene homologous to an endogenous gene of the organism.

In accordance with the present invention, the expression "transgenic" means any cell which includes a nucleic acid sequence which is inserted by artifice into a cell and becomes part of the genome of the organism which develops from that cell. As used herein, the transgenic cells are generally transgenic mammalian cells and the nucleic acid (transgene) is inserted by artifice into the nuclear genome.

In accordance with the present invention, the expression "polypeptide" means any chain of more than two amino acids, regardless of post-translational modification, such as glycosylation or phosphorylation. Polypeptides include proteins, polypeptide fragments thereof, peptide mimetics thereof, and mutants thereof.

In accordance with the present invention, the expression "apoptotic fragment" means a polypeptide fragment of an E4 death protein (i.e., E4orf4 and E4orf6) that has a transformed cell-killing ability that is 75%, more preferably 95%, or most preferably, 100% or greater when compared to the transformed cell-killing ability of the full length protein.

In accordance with the present invention, the expression "substantially pure polypeptide" means a polypeptide that has been separated from the components that naturally accompany it. Typically, the polypeptide is substantially pure when it is at least 60%, by weight, free from the proteins and naturally-occurring organic molecules with which it is naturally associated. Preferably, the polypeptide is an E4 death protein polypeptide that is at least 75%, more preferably at least 90%, and most preferably at least 99%, by weight, pure. A substantially pure E4 death protein polypeptide may be obtained, for example, by extraction from a natural source (e.g. an adenovirus) by expression of a recombinant nucleic acid encoding an E4 death protein polypeptide, or by chemically synthesizing the protein. Purity can be measured by any appropriate method, e.g., by column chromatography, polyacrylamide gel electrophoresis, or HPLC analysis.

A protein is substantially free of naturally associated components when it is separated from those contaminants which accompany it in its natural state. Thus, a protein which is chemically synthesized or produced in a cellular system different from the cell from which it naturally originates will be substantially free from its naturally associated components. Accordingly, substantially pure polypeptides include those derived from adenoviruses but synthesized in E. coli or other prokaryotes. By "substantially pure nucleic acid" is meant nucleic acid (e.g., DNA) that is free of the genes which, in the naturally-occurring genome of the organism from which the DNA of the invention is derived, flank the gene. The term therefore includes, for example, a recombinant DNA which is incorporated into a vector; into an autonomously replicating plasmid or virus; or into the genomic DNA of a prokaryote or eukaryote; or which exists as a separate molecule (e.g., a DNA or a DNA fragment produced by PCR or restriction endonuclease digestion) independent of other sequences. It also includes a recombinant DNA which is part of a hybrid gene encoding additional polypeptide sequence.

In accordance with the present invention, the expression "specifically binds" is meant an antibody that recognizes and binds a protein but that does not substantially recognize and bind other molecules in a sample, e.g., a biological sample, that naturally includes protein. Preferably, the specifically binding antibody which specifically binds an adenovirus protein (e.g., E4orf4) does not bind another adenovirus protein (e.g., E4orf6).

In accordance with the present invention, the expression "analog" includes, without limitation, polypeptide fragments, peptide and non-peptide mimetics, reagents and compounds which mimic the cell killing function, and reagents and compounds which mimic other functions of E4orf4 or E4orf6 proteins.

In accordance with the present invention, the expression "pharmaceutically acceptable carrier" means a carrier which is physiologically acceptable to the treated mammal while retaining the therapeutic properties of the compound with which it is administered. One exemplary pharmaceutically acceptable carrier is physiological saline. Other physiologically acceptable carriers and their formulations are known to one skilled in the art and described, for example, in Remington's Pharmaceutical Sciences, (18$^{th}$ edition), ed. A. Gennaro, 1990, Mack Publishing Company, Easton, Pa.

In accordance with the present invention, the expression "viral vector" means a strand of DNA which includes elements taken from a virus. Viral vectors may direct the expression of inserted DNA from an exogenoous promoter, or may direct expression of inserted DNA from the vector's own long terminal repeat (LTR) sequences. Preferable viral vectors are able to be packaged in non-lytic viruses capable of infecting cells which then expressed the DNA inserted into the viral vector.

The pharmaceutical agent of the present invention allows for the selective killing of cells that are prevented from dying by a virus or as a consequence of a disease state. Thus, the pharmaceutical agent of the present invention only kills the inappropriately surviving cells, such as cancer cells or viral infected cells. This results in a substantially side effect free therapy for the patient.

The pharmaceutical agent of the present invention includes, without limitation, E4 death proteins of any adenovirus of any serotype, fragment thereof, and peptide and non-peptide mimetics of these protein products.

BRIEF DESCRIPTION OF THE DRAWINGS

FIG. 1B summarizes relevant adenovirus mutants;

FIG. 15 shows the nucleic acid (top) (SEQ ID NO.: 1) and amino acid (bottom) (SEQ ID NO.: 2) sequences of Adenovirus type 5 (Ad5) E4orf6; and FIG. 16 shows the nucleic acid (top) (SEQ ID NO.: 3) and amino acid (bottom) (SEQ ID NO.: 4) sequences of Adenovirus type 5 (Ad5) E4orf4.

DETAILED DESCRIPTION OF THE INVENTION

We have discovered that in the absence of E1B, E1A open reading frame (orf) protein products also induce p53-independent apoptosis. Our results indicate that such apoptotic cell death is only induced by the 289R E1A protein. Furthermore, when p53-null mouse cells constitutively expressing E1A products are infected by an adenovirus vector lacking the entire E1A and E1B coding regions but containing early regions E2, E3 and E4, rapid cell death due to apoptosis is observed. Furthermore, we show that 289R induces apoptosis in p53-null mouse and human cells, and that such p53-independent cell death requires the expression of another early viral gene. In the present invention, we describe genetic analyses which indicate that neither E2 nor E3 products are necessary for p53-independent cell death and that two E4 proteins are responsible for p53-independent cell death induced by the 289R E1A product. These results indicate that the role of E1A-289R may be to transactivate expression of an additional early transcript whose product actually induces p53-independent apoptosis. We provide herein that two E4 gene products are responsible for such cell killing and therapeutic compositions, methods, and drug screens which stem from this discovery.

We show that both the E1B-19 kDa protein and cellular Bcl-2 inhibit or significantly delay53-independent apoptosis. Neither early regions E2 or E3 appear to be necessary for such cell death. Analysis of a series of E1A mutants indicates that mutations in the transactivation domain and other regions of E1A correlate with E1A-mediated transactivation of E4 gene expression. Furthermore, p53-deficient human Saos-2 cells infected with a mutant adenovirus which expresses E1B but none of the E4 gene products remains viable for a considerably longer period of time than p53-deficient human Saos-2 cells infected with wild-type (wt) Ad5. In addition, an adenovirus vector lacking both E1 and E4 is unable to induce DNA degradation and cell killing in E1A-expressing cell lines. These data showed that an E4 product was essential for E1A-induced p53-independent apoptosis.

The following examples are meant to illustrate the invention and do not limit the invention.

I. Materials and Methods Used in the Present Invention

Cells and Viruses

Figure 1A:
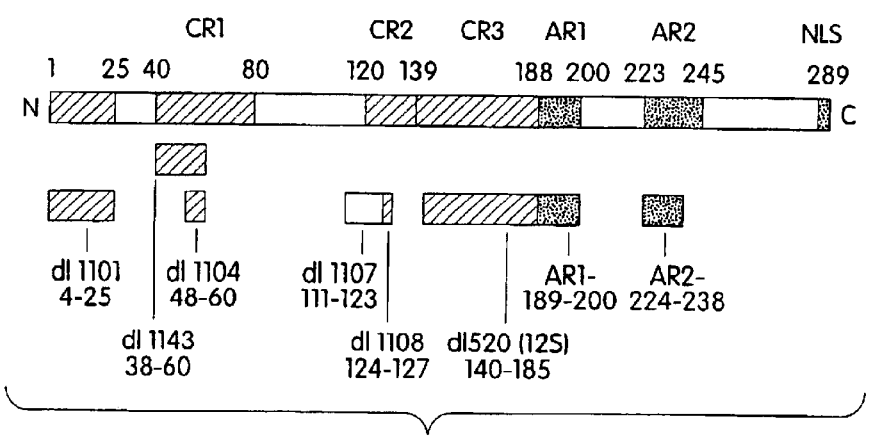
FIG. 1A shows the regions encoding amino acid sequences of the Ad5 E1A proteins and mutants thereof.

Human Saos-2 cells (ATCC HTB 85) and 10(1) mouse embryo fibroblast-derived cells, which are both deficient for p53 expression, were cultured in 60 mm-diameter dishes (Corning Glass Works, Coming, N.Y.) in Dulbecco's modified MEM (DMEM) supplemented with 10% fetal calf serum (FCS) as were both NIH-3T3 and CHO cells. The cell line Saos-2/Bcl-2(3g4), which stably expresses, Bcl-2, was derived for this study from Saos-2 cells by selection with G418, as was the control line Saos-2/Neo(2a2). 1A.A3, 1A.A6 and 1A.A12 mouse embryo fibroblast (MEF) cell lines expressing Ad5 E1A proteins, and Hy.A3 hygromycin-selected control lines, have been described previously (Lowe, S. W. et al., 1994, Proc. Natl. Acad. Sci. U.S.A. 91: 2026–2030), and were cultured in DMEM containing 10% FCS and 100 mg/mL of hygromycin. Normally cells were infected with mutant or wild-type (wt) Ad5 at a multiplicity of 100 pfu per cell. Ad5 E1A mutants are illustrated in FIG. 1A and include deletion mutants dl1101 (residues 4–25 deleted), dl1143 (38–60), dl1107 (111–123), dl1108 (124–127), dl1143/08 (38–60 plus and dl1132 (224–238). Proteins encoded by some of the mutants used in the present studies have been presented, including the residues removed in deletion mutants. CR1, CR2, CR3, AR1 and AR2 have also been indicated. A new E1A mutant termed AR1⁻/E1B⁻, which lacks the entire AR1 region (residues 189–200) and also fails to express E1B products, was generated following the methods previously described in Dumont, D. J. et al. (J. Virol. 63: 987–991, 1989). Further mutants were generated according to standard molecular biology techniques. Mutant AR2⁻/E1B⁻ was generated by introducing dl1132, which lacks residues 224–238, into a background that fails to express E1B proteins. Mutant AR1⁻/AR2⁻/E1B represents a combination of the latter two mutants. Additional E1A mutants containing single amino acid substitutions at various sites within CR3 were produced by subcloning appropriate restriction enzyme fragments from mutant E1A cDNA plasmids into genomic viral DNA, followed by rescue into virus to form mutants AD147VL (Val-147 converted to Leu), AD177CS, and AD I85SG. All other mutants have been summarized in FIG. 1B, which is a list providing the names and defects of E1B and other mutants. Two mutants fail to express E1B proteins of 19 kDa (originally termed pm 1716/2072 but now called E1B/19K⁻) and 55 kDa (originally pm2019/2250, now E1B/55K⁻) (McLorie, W. et al., supra). Mutant 12S/E1B⁻ (originally d/520E1B,) produces only the E1A-243R protein encoded by the 12S mRNA and no E1B products. Mutant E1B⁻ which expresses both major E1A products but neither the 19 kDa or 55 kDa E1B species was described previously (Teodoro, J. G. et al., 1995, Oncogene 11:467–474). A mutant that expresses only 289R in the absence of E1B, termed 13S/E1B⁻, was similarly prepared for the present studies. A series of E1A mutants (dl110I/E1B⁻, dl1107/E1B, AD147VL/E1B⁻, etc.), which express no E1B products, was also produced by introducing E1A mutations into mutant E1B⁻, which expresses both 289R and 243R E1A products but no E1B (Teodoro, J. G. et al., 1995, Oncogene 11: 467–474). The presence of mutations in all mutants was confirmed by DNA sequencing, restriction enzyme digestion, or Southern blotting, all of which are standard molecular biology techniques. Further Ad5 vectors used in this study included AdLacZ in which the E1 (E1A+E1B) region was replaced with the *E. coli* gene lacZ under the CMV promoter, and Ad5dl70-8 (F.L. Graham, McMaster University, Hamilton, Ont., Canada), which was generated by cotransfection of plasmids pAB7 and pBHG10, as described previously (Bett, A. J., 1994, Proc. Natl. Acad. Sci. USA, 91:8802–8806), and which lacks both E1 and the entire E3 region. These viral vectors and other E1A and E1B mutants were grown on human 293 cells, as has been previously described (Graham, F. L. et al., 1977, J. Gen. Virol. 36: 59–72; Bett, A. J., 1994; Proc. Natl. Acad. Sci. USA, 91:8802–8806). Adenovirus vector AdRSVβgal. 11, which lacks the entire E1 and E4 regions, was a gift of Douglas Brough (GenVec, Rockville, Md.). In addition, some experiments were carried out with human adenovirus type 2 (Ad2) mutant dl1019 which contains deletions that eliminate expression of all E4 products and which was propagated on W162 monkey cells, as described previously (Bridge, E. et al., 1989, J. Virol. 63: 631–638). Other E4 mutants (Bridge, E. et al., supra) have been summarized in FIG. 10.

DNA Fragmentation

Low molecular weight DNA was isolated from mock- or Ad5-infected cells as described in Teodoro et al. (Oncogene 11:467–474, 1995). For these experiments, 60 mm-diameter plates of cells were harvested at 40 hours post-infection and lysed in pronase lysis buffer (10 mM Tris-HCl (pH 8) containing 5 mM EDTA, 100 mM NaCl, and 1 mg/mL (w/v) pronase to which SDS was added to 0.5% w/v). Cell lysates were next incubated at 37° C. for 2 hours and NaCl was then added to a final concentration of 1M. Samples were then incubated overnight at 4° C. and centrifuged at 15,000×g for 30 min. Extracted nucleic acids were treated with RNAase A and analyzed on 1% agarose gels stained with ethidium bromide.

Cell Viability Assays

Cells were infected with wt or mutant virus in 24-well plates containing cells at about 80% confluence. At various times following infection adherent and non-adherent cells were pooled and viability was assessed by Trypan Blue™ exclusion. At least 300 cells were counted at each time point.

Measurement of E1A-Mediated Transactivation of the Adenovirus E4 Promoter

CAT transactivation assays were performed using NIH 3T3 or CHO cells plated at a density of $2 \times 10^5$ cells on 60 mm-diameter dishes. The E4 CAT reporter plasmid (E4-CAT) contained the E4 promoter upstream of the chloramphenicol acetyltransferase (CAT) gene. Transient cotransfections were performed by the calcium phosphate precipitation method (described, for example, in Ausubel, F. et al., 1994, *Current Protocols in Molecular Biology*, John Wiley & Sons, New York, N.Y.) using 2.5 μg of reporter plasmid DNA and 2.5 μg of DNA from plasmids expressing wt or mutant E1A products. Cells were glycerol shocked 12 hours after transfection and then harvested 36 hours later. CAT assays were performed using cell extracts containing equal amounts of β-galactosidase activity, as has been described (Ausubel, F. et al., supra). The amount of activity was quantified from TLC plates using a Fujix Bas 2000™ Phosphorimager.

Luciferase Death Assay

The E4 open reading frames (orfs) were individually cloned into the pCDNA3.1 plasmid (commercially available from Invitrogen) which drives gene expression with the CMV promoter. The plasmids were purified using 2×CsCl purification and transfections were done by calcium phosphate precipitation. Each E4orf-encoding plasmid was transfected together with a plasmid expressing the luciferase gene under the control of the RSV promoter (pRSV-luciferase). Either the empty pCDNA vector or a pCDNA vector encoding crmA was used as a negative control for cell killing.

II. E1A-induced p53-Independent Apoptosis is Inhibited by Both the E1B-19 kDa Protein and Cellular Bcl2

Figure 2:
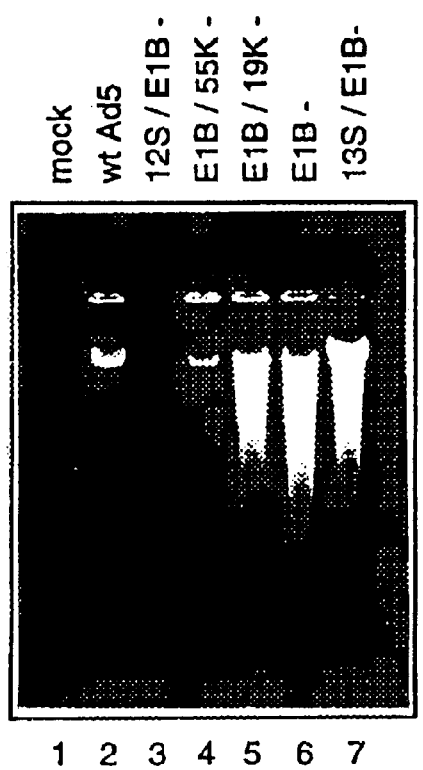
FIG. 2 is an agarose gel analysis of the induction of DNA fragmentation by indicated Ad5 mutants in p53-null 10(1) cells.

We have recently shown that whereas both major Ad5 E1A products could induce apoptosis in cells expressing p53, only the 289R E1A protein could do so in cells lacking p53 (Teodoro, J. G. et al., 1995, Oncogene 11: 467–474). FIG. 2 shows the pattern of DNA fragmentation in p53-mouse 10(1) cells infected by various Ad5 mutants. 10(1) cells, which fail to express p53, were infected with various Ad5 mutants, or they were mock-infected, and at 40 hours post-infection (p.i.), low molecular weight DNA was analyzed by agarose gel electrophoresis. The contents of individual lanes are as indicated in FIG. 2. Extracts from mock-infected cells (FIG. 2, lane 1) and those infected with wt Ad5 (FIG. 2, lane 2), which expresses E1B products, displayed reduced levels of extracted low molecular weight DNA and little or no degraded DNA, as did those from cells infected with mutant E1B/55K: (FIG. 2, lane 4), which produces the E1B-19 kDa protein but not the E1B-55 kDa product. With cells infected with mutant E1B', which synthesizes both the 289R and 243R E1A proteins but which produces no E1B products (FIG. 2, lane 6), large amounts of DNA were extracted and high levels of nucleosome-sized DNA fragments were evident. Similar results were also obtained with cells infected with E1B/19K⁻ (FIG. 2, lane 5), which produces the E1B-55 kDa species but not the 19 kDa protein. Induction of DNA degradation in these p53 cells did not occur following infection with 12S/E1B⁻ (FIG. 2, lane 3), which produces only E1A-243R and no E1B, but it did occur with 13S/E1B⁻ (FIG. 2, lane 7), which yields only E1A-289R in the absence of E1B products. Thus, E1A-289R, but not 243R, induced p53-independent apoptosis in the absence of E1B proteins. In addition, these results indicated that the E1B 19 kDa polypeptide but not the 55 kDa E1B product was able to protect against apoptosis induced by E1A in the absence of p53.

Figure 3A:
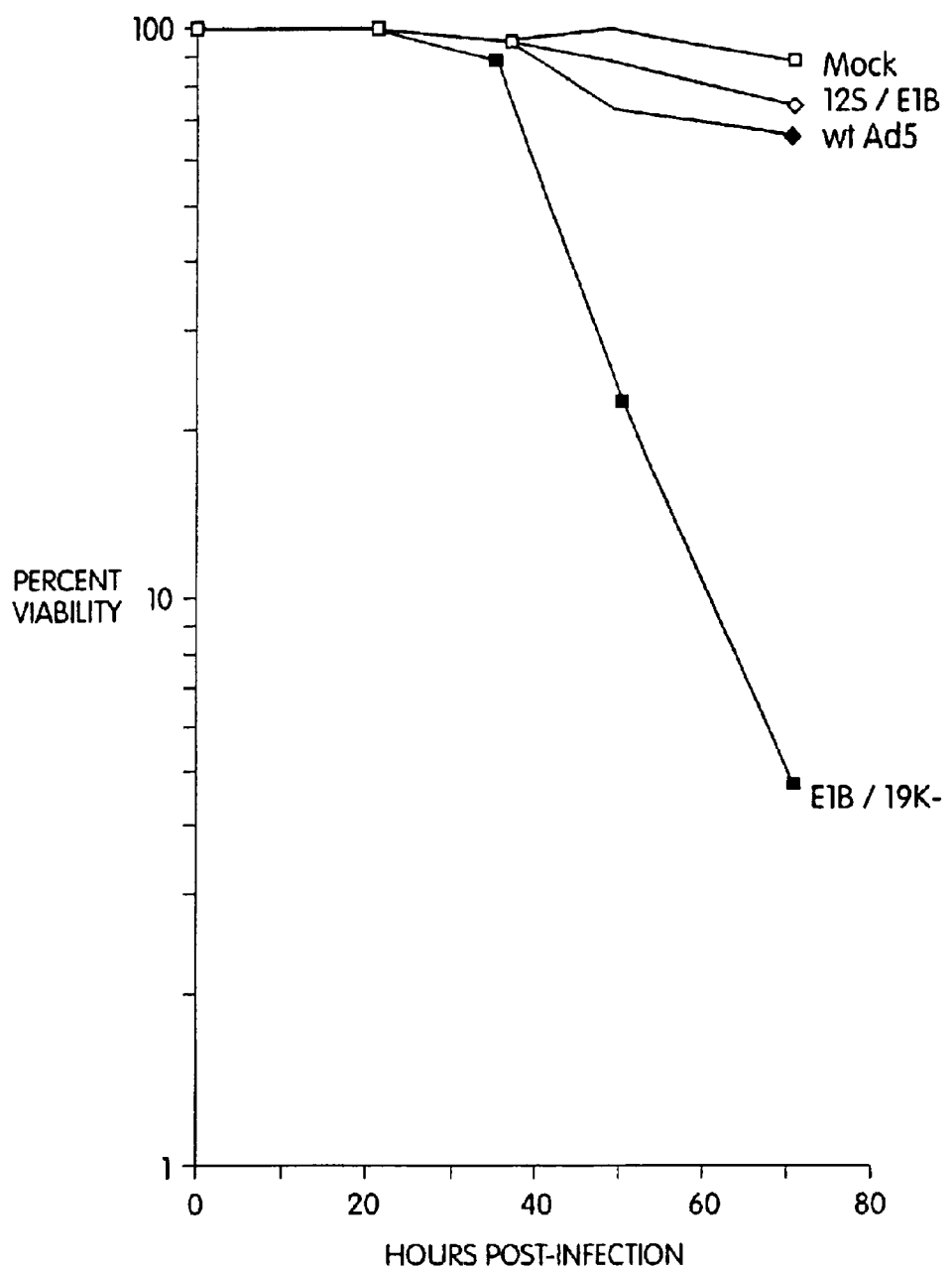
FIGS. 3A and 3B are graphs of the Trypan Blue™ exclusion analyses showing viability of p53-null Saos-2 cells (FIG. 3A) and p53-null Saos-2 cells expressing Bcl-2 (FIG. 3B) infected with indicated Ad5 mutants.
Figure 3B:
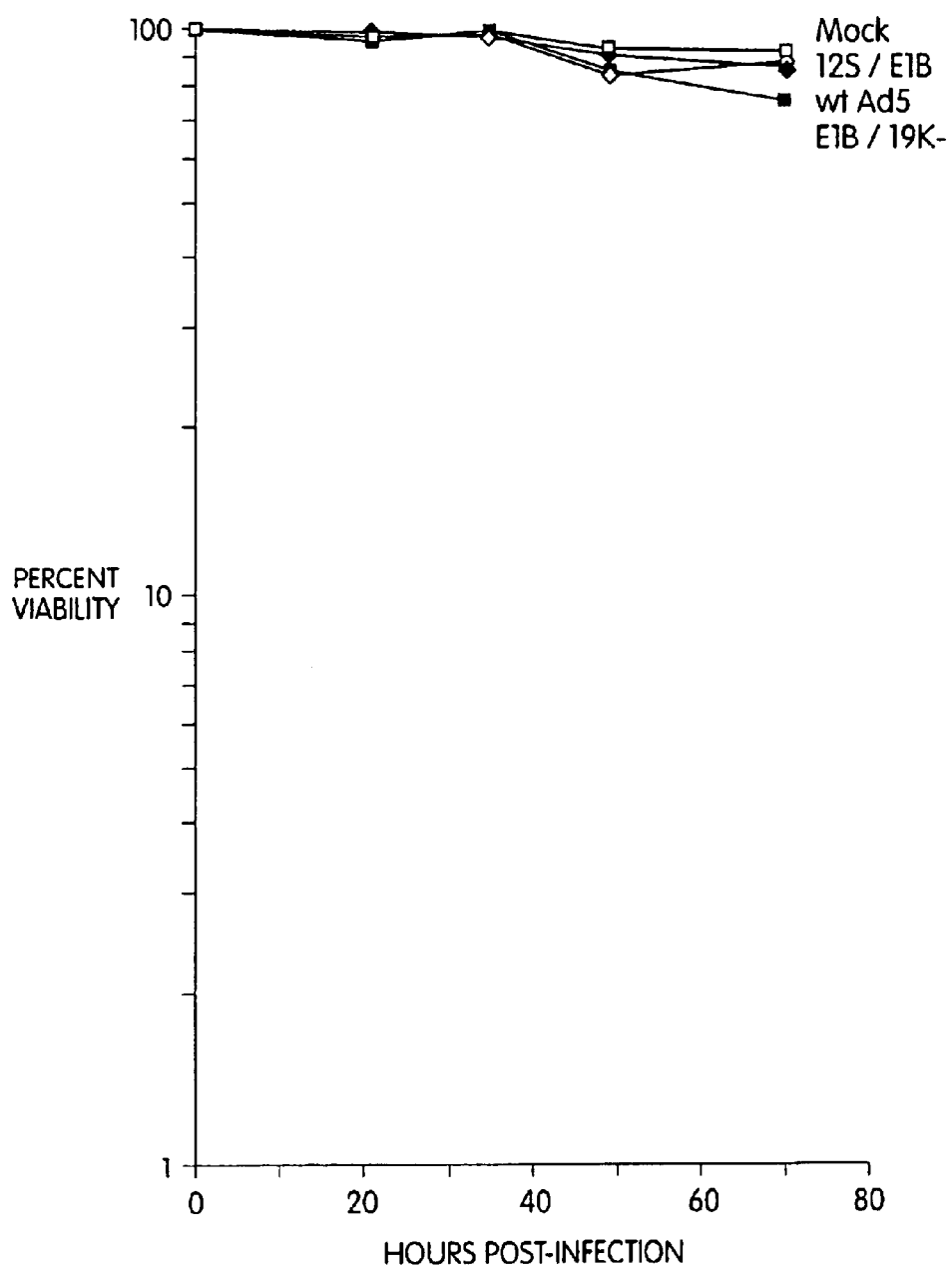

To examine the specificity of inhibition of apoptosis further, studies were conducted to determine if the cellular Bcl-2 protein was also able to prevent p53-independent apoptosis as several previous studies had shown that Bcl-2 and the E1B-19 kDa protein may be functionally similar (Nguyen, M. et al., 1994, J. Biol. Chem. 269: 16521–16524). Human Saos-2 cells, which are defective for synthesis of p53, were transfected with cDNAs encoding the human Bcl-2 protein and the neomycin resistance marker and several cell lines were selected using G418. One such Bcl-2 expressing clone, termed Saos-2/Bcl-2(3g4), and a control Saos-2 clone, Saos-2/neo(2a2) selected only for resistance to G418, were infected with wt Ad5, mutants 12S/E1B⁻ or E1B/19K⁻, or were mock-infected, and cell viability assays were conducted at various times after infection. P53-deficient human Saos-2/neo(2a2) cells (FIG. 3A) or Saos-2/Bcl-2(3g4), which express human Bcl-2 constitutively (FIG. 3B), were mock-infected or infected with wt, E1B/19K or 12S/E1B⁻ and were tested for viability by a Trypan Blue™ exclusion assay at various times following infection. Results have been presented as the logarithm of the % viable cells, and symbols are as indicated in FIGS. 3A and 3B. FIG. 3A shows that Saos-2/neo(2a2) control cells were killed by the E1B/19K virus that expresses E1A-289R, but those infected with wt or 12S/E1B remained almost as viable as mock-infected cells during the test period. FIG. 3B shows that with Saos-2/Bcl-2(3g4) cells which stably express high levels of Bcl-2, little cell death was induced by the E1B/19K⁻ virus. Similar results were obtained with three other control and Bcl-2 producing Saos-2 cell lines. Thus, like the E1B-19 kDa protein, Bcl-2 also blocks E1A-induced p53-independent apoptosis.

III. Role of E1A Domains In p53-independent Apoptosis

Figure 4:
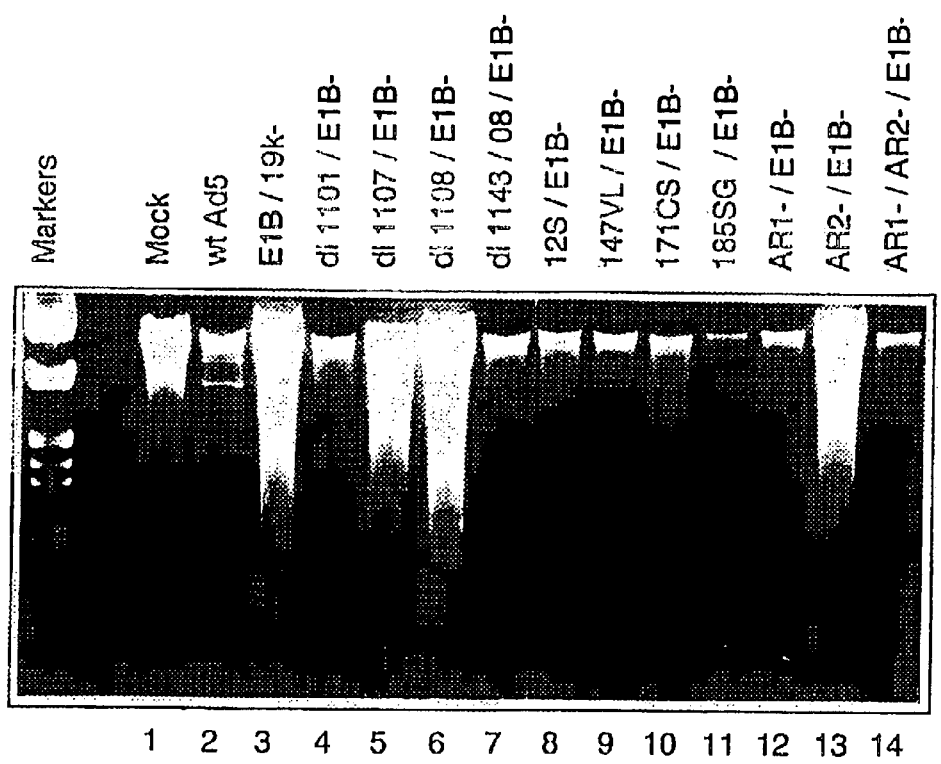
FIG. 4 is an agarose gel analysis of the induction of DNA fragmentation by indicated E1A mutants in p53-null 10(1) cells.
Figure 5:
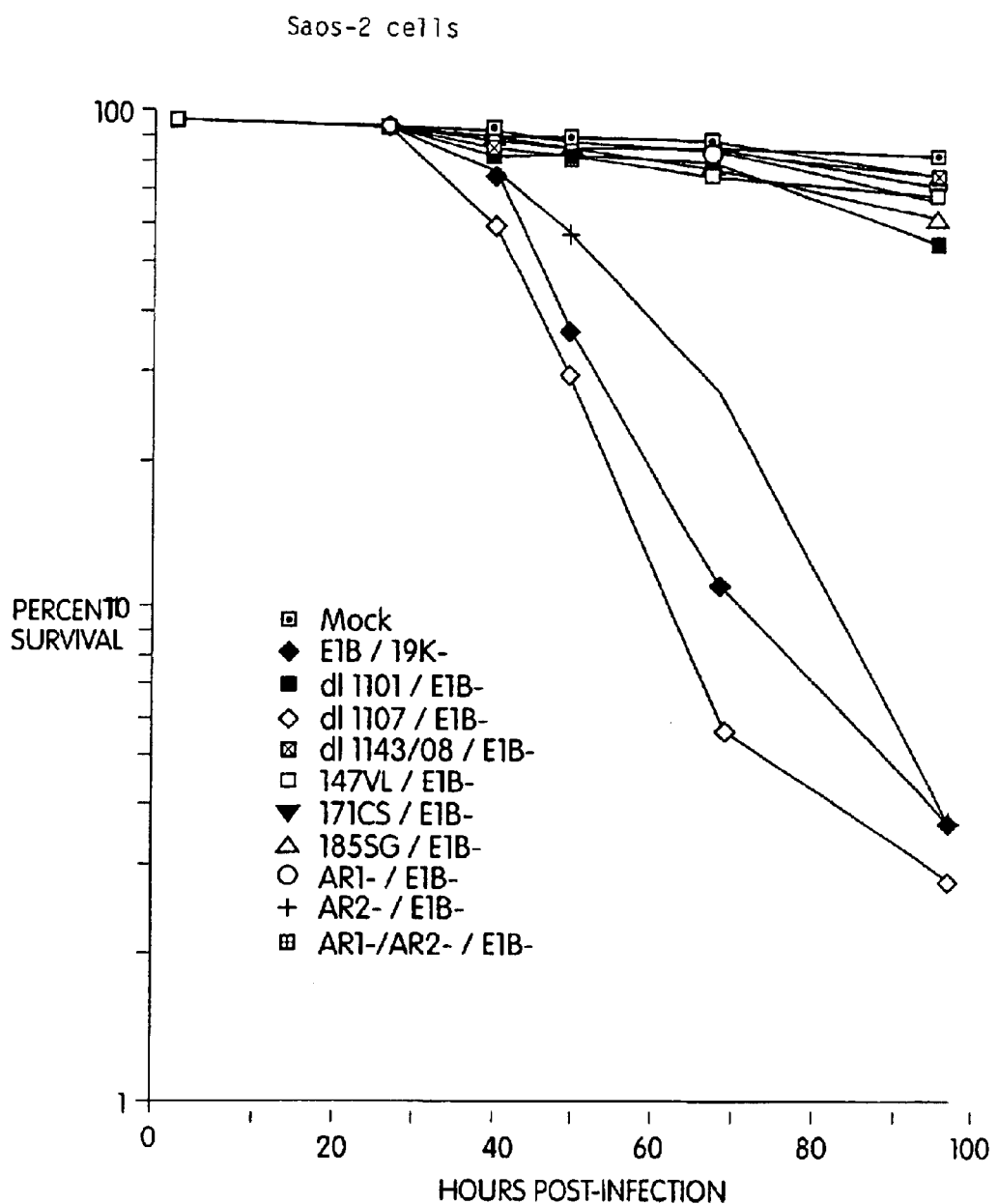
FIG. 5 is a graph of the Trypan Blue™ exclusion analysis showing viability of p53-null Saos-2 cells infected with indicated E1A mutants.

To investigate the regions of E1A products involved in causing p53-independent cell death, p53⁻ mouse 10(1) cells were infected with Ad5 mutants which fail to express E1B and which harbor a variety of defects at various regions of the E1A molecule. Extracts were harvested and analyzed on gels to determine the extent of degradation of low molecular weight DNA. An experiment in p53-deficient 10(1) cells was performed using a series of Ad5 E1A mutants defective in expression of E1B products. 10(1) cells were infected with various Ad5 mutants, or they were mock-infected, and at 40 hours p.i., low molecular weight DNA was analyzed by agarose gel electrophoresis. The contents of individual lanes are as indicated in FIG. 4. FIG. 4 again shows that mutant E1B/19K⁻ (FIG. 4, lane 3) induced DNA degradation whereas such DNA degradation did not occur with wt Ad5 (FIG. 4, lane 2) or mock-infected cells (FIG. 4, lane 1). Mutants which affected the E1A transactivation function associated with CR3 all failed to induce DNA degradation. These included 12S/E1B⁻ (FIG. 4, lane 8), and point mutants AD147VL/E1B⁻, AD171CS/E1B⁻ and AD185SG/E1B⁻ (FIG. 4, lanes 9 to 11, respectively) which carry single residue substitutions at critical residues in CR3 that eliminate E1A transactivation activity. In addition, deletion of AR1 or both AR1 and AR2 (AR1⁻/E1B⁻and AR1/AR2/E1B⁻ in FIG. 4, lanes 12 and 14, respectively) also eliminated DNA degradation whereas removal of AR2 alone (AR2⁻/E1B⁻ in FIG. 4, lane 13) had little effect on eliminating DNA degradation. Interestingly, mutants in CR2 which eliminate complex formation with pRB and related proteins (dl1107/E1B⁻ and dl1108/E1B in FIG. 4, lanes 5 and 6, respectively) had no effect on the induction of DNA degradation, whereas those that eliminated binding of p300 by removal of the N-terminus (dl1101/E1B in FIG. 4, lane 4) or a portion of CR1 as well as the pRB binding site (dl1143/08/E1B⁻ in FIG. 4, lane 7) no longer caused this DNA degradation effect. These results suggested that E1A-induced p53-independent apoptosis required the CR3 transactivation domain, AR1, and the regions necessary for binding of p300 but not pRB-related proteins. FIG. 5 shows that similar results were obtained with these mutants in cell killing assays. An experiment was carried out in which Saos-2 cells were infected with various adenovirus mutants or mock-infected and were then tested for viability by a Trypan Blue™ exclusion assay at various times following infection. Results have been presented as the logarithm of the % viable cells, and symbols are as indicated in FIG. 5. Cell death was induced by the E1B/19K⁻ virus, which expresses both E1A products, and by dl1107/E1B⁻. Mutant AR2⁻/E1B⁻, which lacks AR2, also killed, but was consistently less toxic than the former viruses. All other mutants affecting CR3, AR1 and the p300 binding sites failed to kill significantly during the test period.

IV. Activation of E4 Expression and Apoptosis

Studies were carried out to examine the pattern of E1A transactivation of the E4 promoter in which plasmid DNA encoding various mutants forms of E1A-289R was co-transfected into NIH-3T3 or CHO cells along with DNA from E4-CAT, a construct that encodes CAT under the control of the Ad5 E4 promoter. Table 1 shows that in addition to CR3, activation of the E4 promoter required AR1 and to some extent AR2.

TABLE 1

E4 Transactivation by E1A Mutants

| E1A Mutant | Mutation | Region Affected | E4 CAT* Activity (% wt +/− S.D.) |
|---|---|---|---|
| wt | none | none | 100 |
| dl1101 | Δ4–25 | N-terminus | 30 +/− 11 |
| dl1104 | Δ48–60 | CR1 | 40 +/− 5 |
| dl11107 | Δ111–123 | CR2 | 85 +/− 5 |
| dl1108 | Δ124–127 | CR2 | 81 +/− 14 |
| dl1520 | Δ140–185 | CR3 | 10 +/− 7 |
| AR1⁻ | Δ189–200 | AR1 | 25 +/− 7 |
| AR2⁻ (pm1132) | Δ224–238 | AR2 | 64 +/− 16 |

*CHO or 3T3 cells were transfected with plasmid DNA encoding various E1A mutants and CAT under the Ad5 E4 promoter.

Cell extracts were assayed for CAT activity, as described herein. The CAT activity has been expressed as a percentage of that obtained with wt. Three independent assays were done for each mutant.

In addition, regions at the N-terminus and in the CR1 involved in binding of p300 were also found to be of importance in the activation of the E4 promoter. These results closely paralleled the pattern of E1A-induced p53-independent apoptosis and suggested that E4 products might be involved in this p53-independent cell death.

V. E2 and E3 Products Are Not Required for Apoptosis

Given the results described herein outlining the requirements for the E1A-induction of p53-independent apoptosis, we determined that it was unlikely that E2 products were responsible for the induction of p53-independent apoptosis. First of all, in addition to CR3, complex formation involving CR2 and the pRB family of proteins activates E2 expression, and CR2 was shown to be of little importance in cell killing. Secondly, reasonably high levels of expression of E2 proteins are known to be induced by the E1A-243R protein which is completely unable to induce p53-independent apoptosis.

Experiments were next carried out to determine if any E3 products were involved in the induction of p53-independent apoptosis. The 1A.A3 mouse embryo fibroblast cell line lacking p53 but expressing Ad5 E1A proteins, and Hy.A3 hygromycin-selected p53 control cells (Lowe, S. W. et al., 1994, Proc. Natl. Acad. Sci. U.S.A. 91: 2026–2030), were infected with wt Ad5, the E1B/19K⁻ virus, adenovirus vector AdLacZ, which contains lacZ in place of E1A and E1B, or with vector Ad5dl70-8, which lacks both the entire E1 and E3 regions. Cell extracts were then assayed for the presence of degraded DNA.

Figure 6:
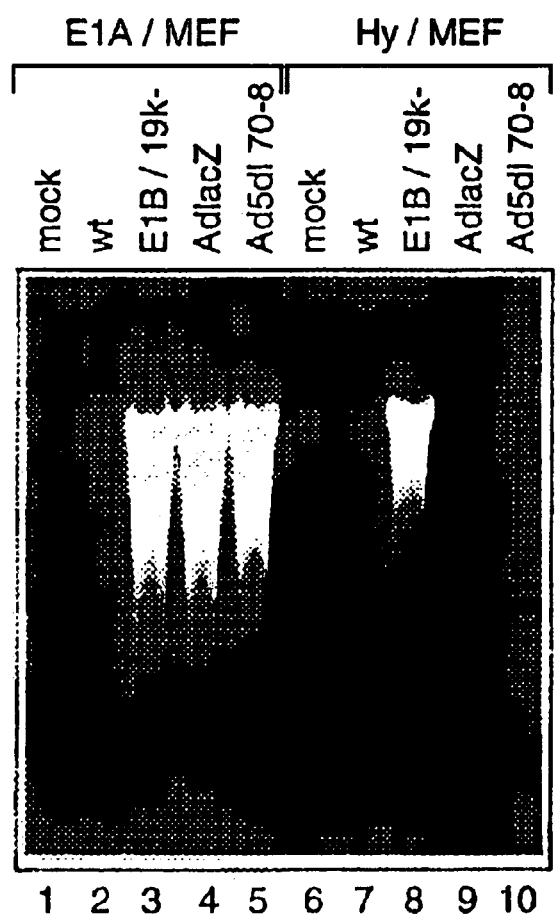
FIG. 6 is an agarose gel analysis of the induction of DNA fragmentation by indicated Ad5 mutants in E1A/MEF and Hy/MEF cells.

Accordingly, cell lines expressing 289R and 243R E1A proteins constitutively (E1A/MEF), or the Hy.A3 (HY/MEF) non-expressing control cell line, were mock-infected or infected with wt Ad5 or adenovirus vectors AdLacZ or Ad5dl70-8. After 40 hours, DNA was extracted and analyzed by agarose gel electrophoresis. The contents of individual lanes are as indicated in FIG. 6. FIG. 6 shows that high levels of DNA degradation were induced in 1A.A3 cells with the 19K⁻ mutants as well as both adenovirus vectors AdLacZ or Ad5dl70-8. FIG. 6 also shows that in the control cells lacking constitutive E1A expression, only the E1B/19K⁻ virus induced DNA degradation. Similar results were also obtained with two other similar E1A-expressing cell lines, 1A.A6 and 1A.A12. These results indicated that E3 products were not required for induction of p53-independent apoptosis by E1A under these conditions.

VI. E4 Proteins are Essential for p53-independent Apoptosis

Figure 7:
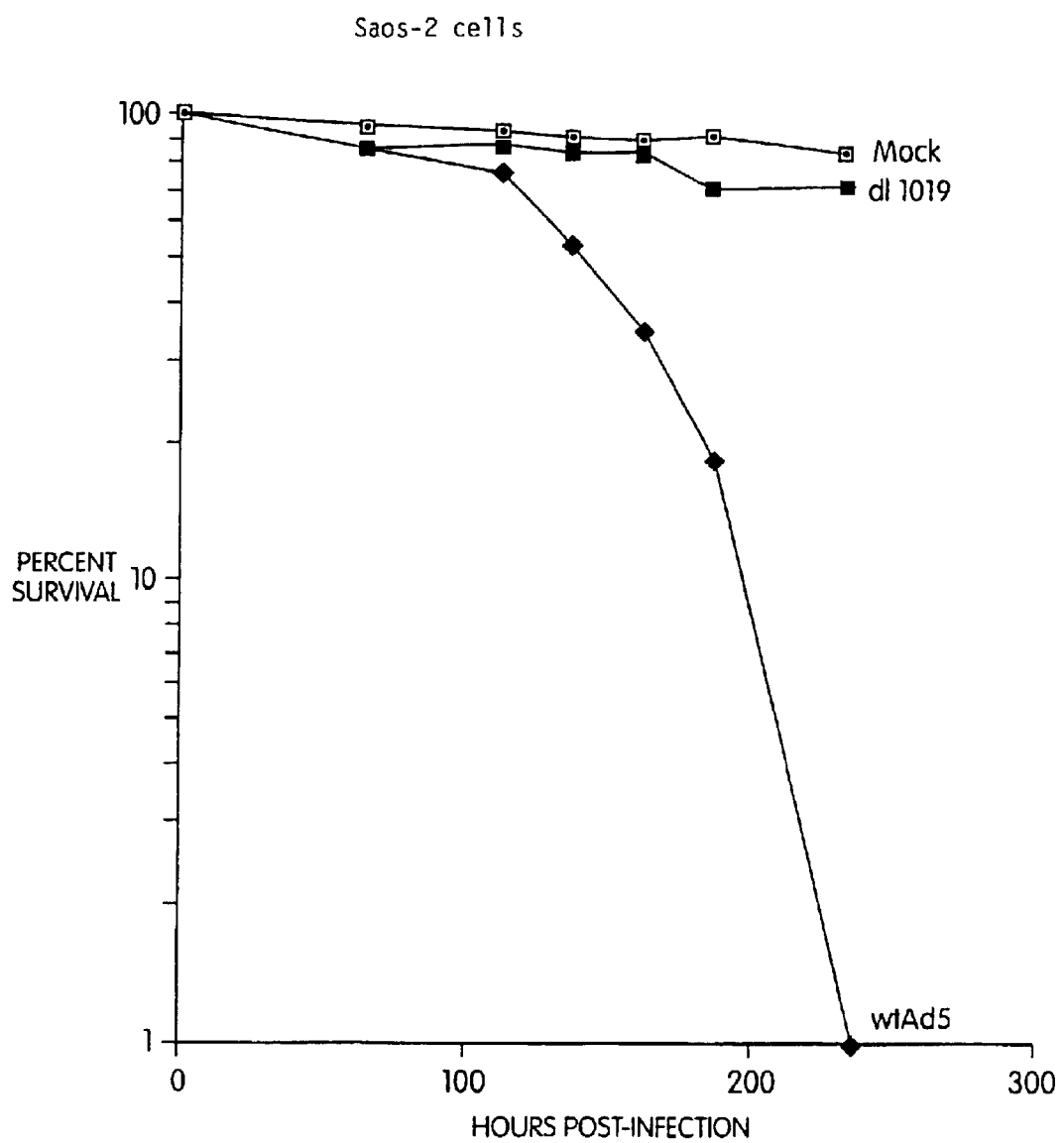
FIG. 7 is a graph of the Trypan Blue™ exclusion analysis showing viability of p53-null Saos-2 cells infected with indicated Ad5 mutants.
Figure 8:
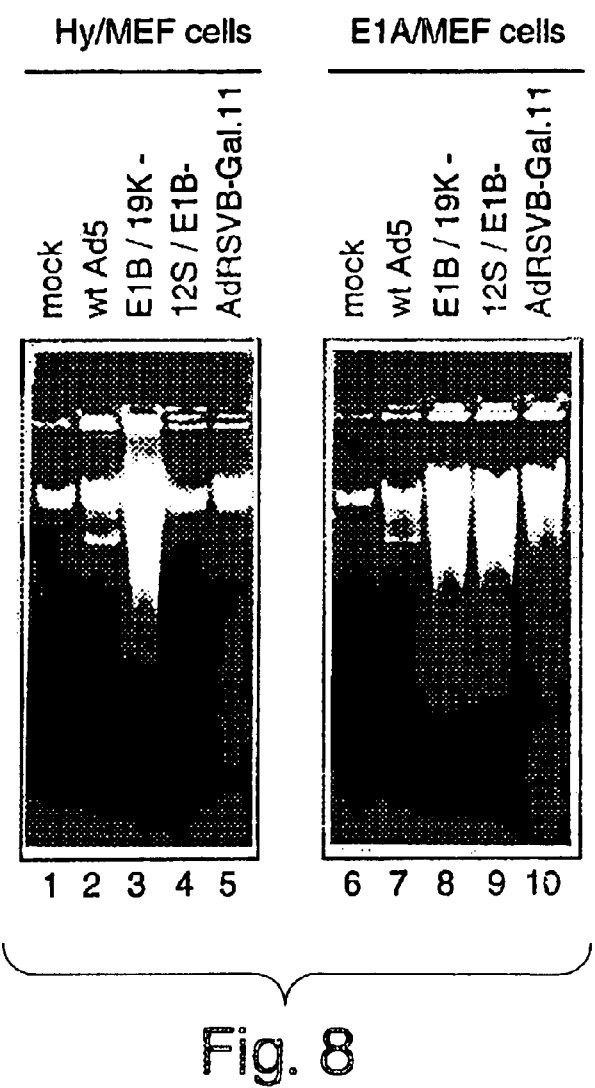
FIG. 8 is an agarose gel analysis of the induction of DNA fragmentation by indicated Ad5 mutants in Hy/MEF and E1A/MEF cells.
Figure 9A:
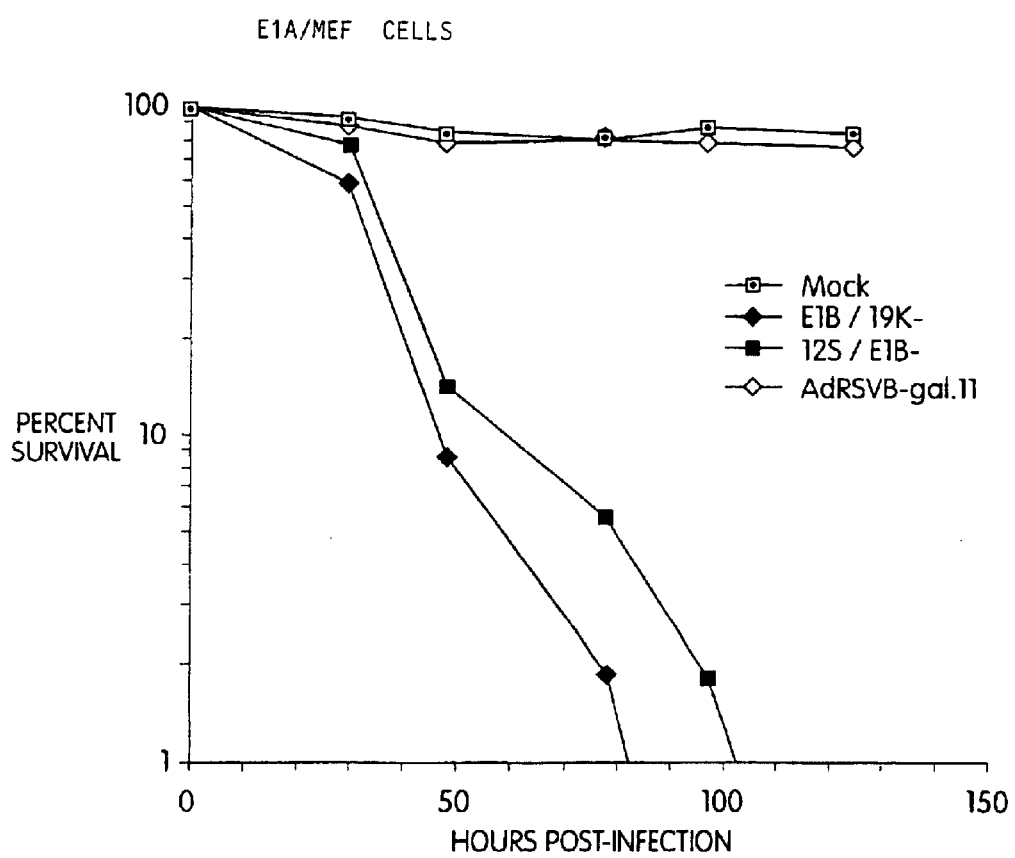
FIGS. 9A and 9B are graphs of the Trypan Blue™ exclusion analyses showing E1A/MEF (FIG. 9A) and Hy/MEF (FIG. 9B) cell killing by indicated Ad5 mutants.
Figure 9B:
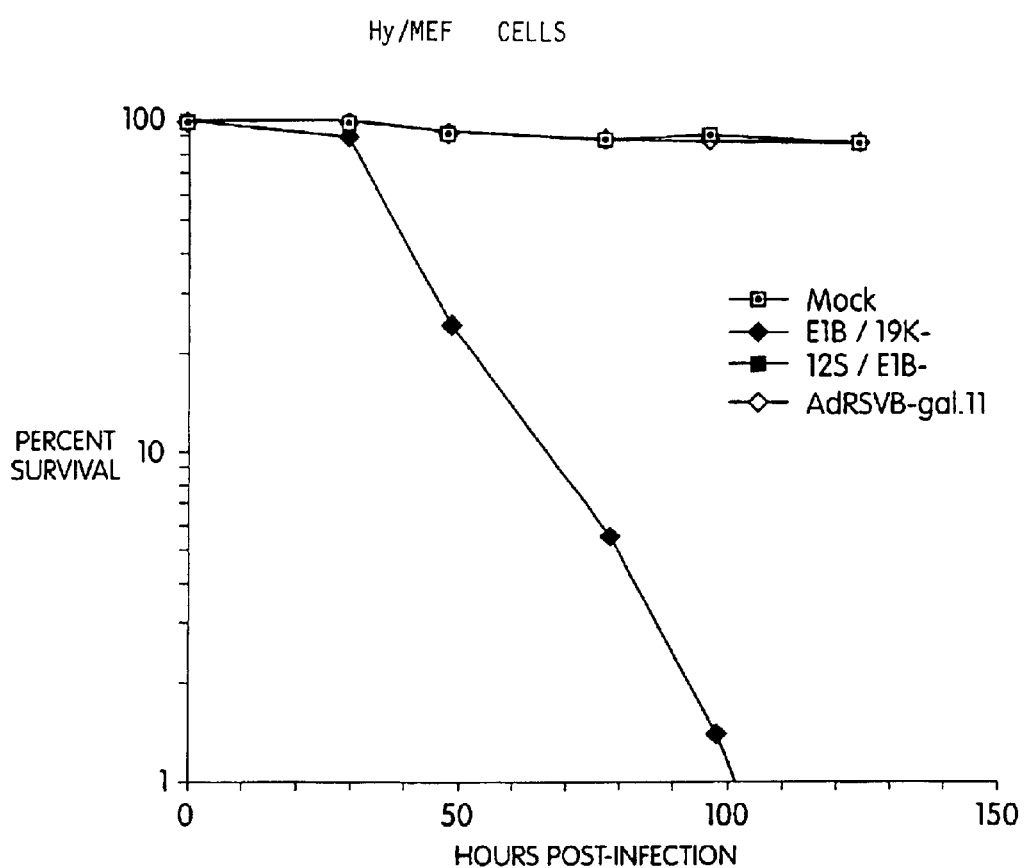

To determine directly if E4 products were involved in the induction of cell death, as suggested by experiments described above, two approaches were taken. In the first approach, human p53⁻ Saos-2 cells were infected with wt Ad5 or wt adenovirus type 2 (Ad2), or with Ad2 mutant dl1019 which produces no E4 proteins (Bridge, E. et al., supra), or they were mock-infected. Although these viruses express E1B proteins and thus are protected from E1A-induced apoptosis, it was thought that if E4 products were essential for p53-independent cell death, some difference in long term cell survival might be observed. Thus, at various times up to 10 days, infected cultures were tested for cell viability. For this experiment, Saos-2 cells were mock-infected or infected with wt Ad5 or Ad2, or dl1019. At various times up to 10 days cell viability was assessed by Trypan Blue™ exclusion. Data have been expressed as % cell viability and symbols are as indicated in FIG. 7. FIG. 7 shows that cells infected by wt Ad5 virus began to die at about 100 hours p.i., and by 240 hours p.i. almost all of the cells were dead. Similar results were obtained with wt Ad2 (adenovirus type 2) infected cells. However, such was not the case with dl1019-infected cells, which remained almost as viable as mock-infected cells even 10 days after infection. These results indicated that an E4 product was involved in cell killing in the absence of p53. This idea was confirmed in experiments involving infection of E1A-expressing p53⁻ 1A.A3 cells with the adenovirus vector AdRSVβgal.11 in which both the E1 and E4 regions had been completely deleted. For this experiment, cell lines expressing 289R and 243R E1A proteins constitutively, or the Hy.A3 non-expresser control cell line, were mock-infected or infected with wt Ad5, E1B/19K⁻, 12S/E1B⁻, or the adenovirus vector AdRSVβgal.11, which lacks both E1 and E4. After 40 hours, DNA was extracted and analyzed by agarose gel electrophoresis. The contents of individual lanes are as indicated in FIG. 8. FIG. 8 shows that in control Hy.A3 (Hy/MEF) p53⁻ cells, which do not express E1A, only the E1B/19K Ad5 mutant caused DNA degradation, and neither wt, 12S/E1B⁻, nor the AdRSVβgal.11 vector had any significant effect (i.e., did not induce DNA degradation). With 1A.A3 cells (E1A/MEF), both the E1B/19K⁻ (FIG. 8, lane 8) and 12S/E1B⁻ (FIG. 8, lane 9) viruses induced DNA degradation, but the AdRSVβgal.11 vector (FIG. 8, lane 10) still had little effect on the induction of DNA degradation. Similar results were obtained with the other two sister cell lines, 1A.A6 and 1A.A 12. The ability of the E1B/19K⁻ and 12S/E1B⁻ viruses to induce apoptosis in 1A.A3 cells was analyzed further in cell killing experiments. Cell lines expressing 289R and 243R E1A proteins constitutively (E1A/MEF—right panel), or the Hy.A3 (Hy/MEF) non-E1A expressing control cell line (left panel), were mock-infected or infected with wt Ad5, E1B/19K⁻, 12S/E1B⁻, or the adenovirus vector AdRSVβgal.11. At various times after infection, cell viability was assessed by Trypan Blue™ exclusion. Data have been expressed as % cell viability and symbols are as indicated in the FIGS. 9A and 9B. FIG. 9B shows that in the Hy.A3 (HY/MEF) control cells, only the E1B/19K⁻ virus induced cell death, whereas in 1A.A3 cells (E1A/MEF—shown in FIG. 9A), both the E1B/19K⁻ and 12S/E1B⁻ viruses did so. However, in both cases the AdRSVβgal.11-infected cells remained as fully viable as mock-infected cultures. These data thus confirmed that an E4 product was responsible for E1A-induced p53-independent cell death.

VII. Identification of Adenovius E4 Death Proteins

Figure 10:
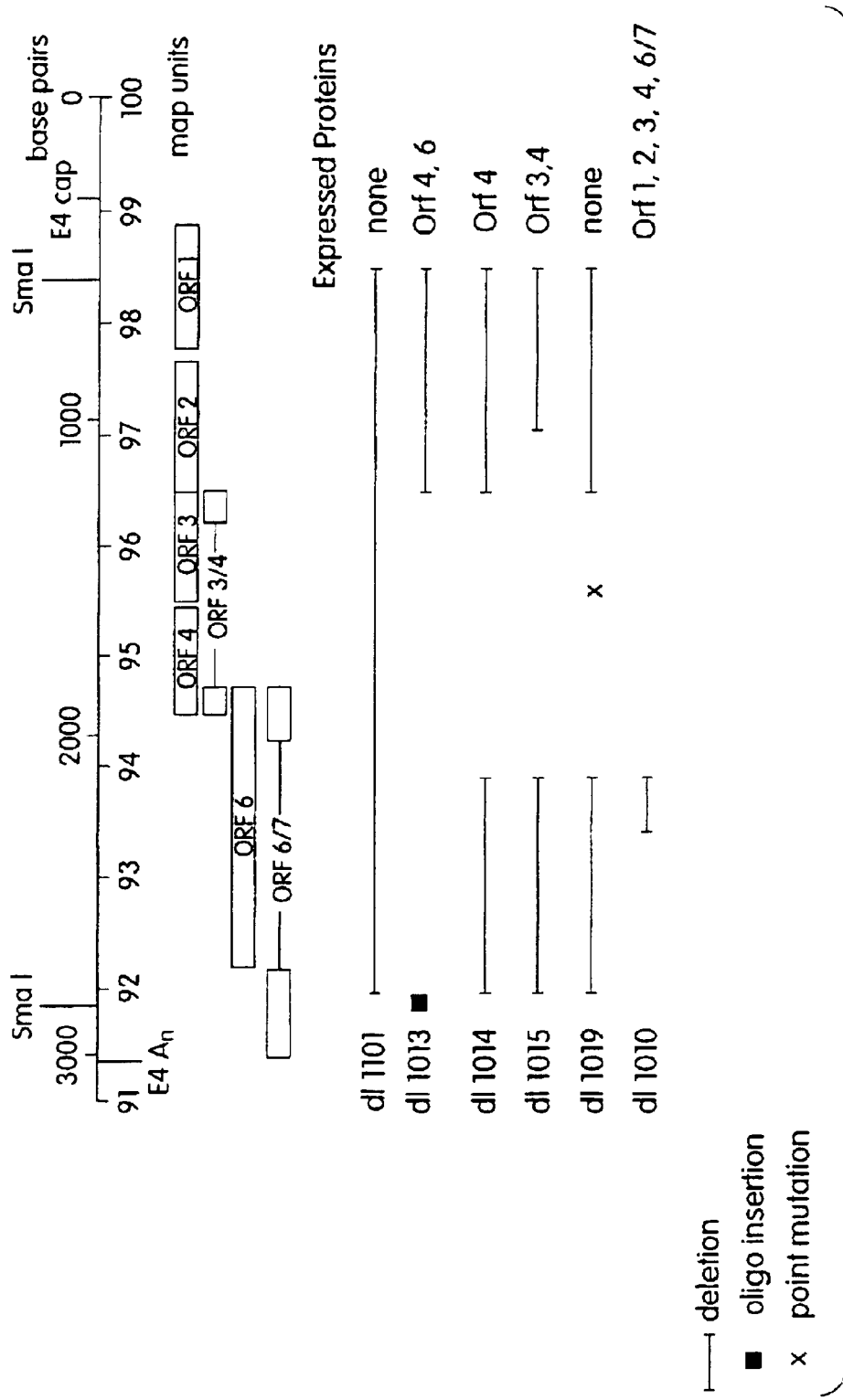
FIG. 10 shows the regions encoding amino acid sequences of the E4orf proteins and indicates E4orf expression in Ad5 mutants.
Figure 11:
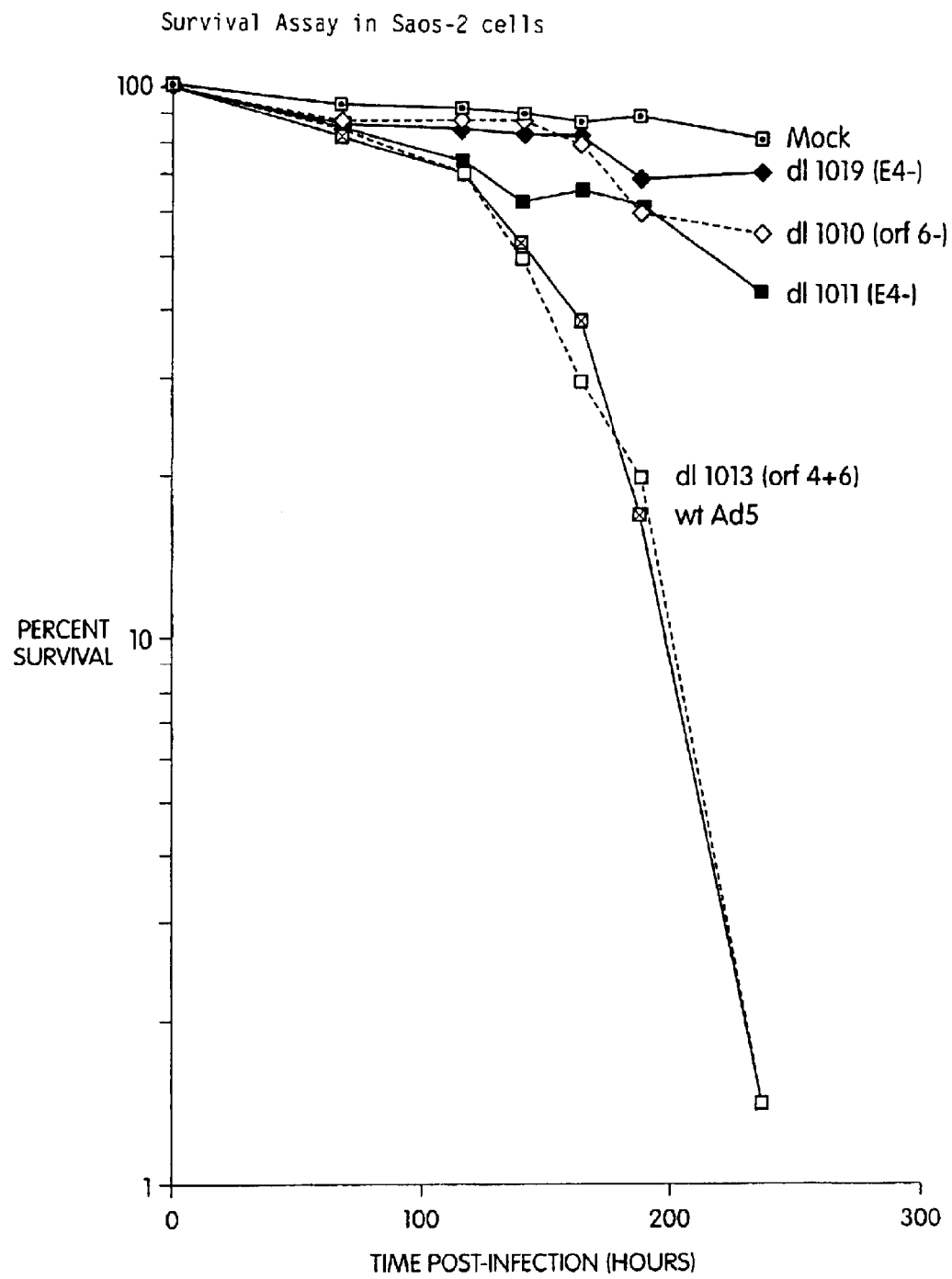
FIG. 11 is a graph of the Trypan Blue™ exclusion analysis showing the role of E4orf6 in p53-independent cell killing (in p53-null Saos-2 cells)
Figure 12:
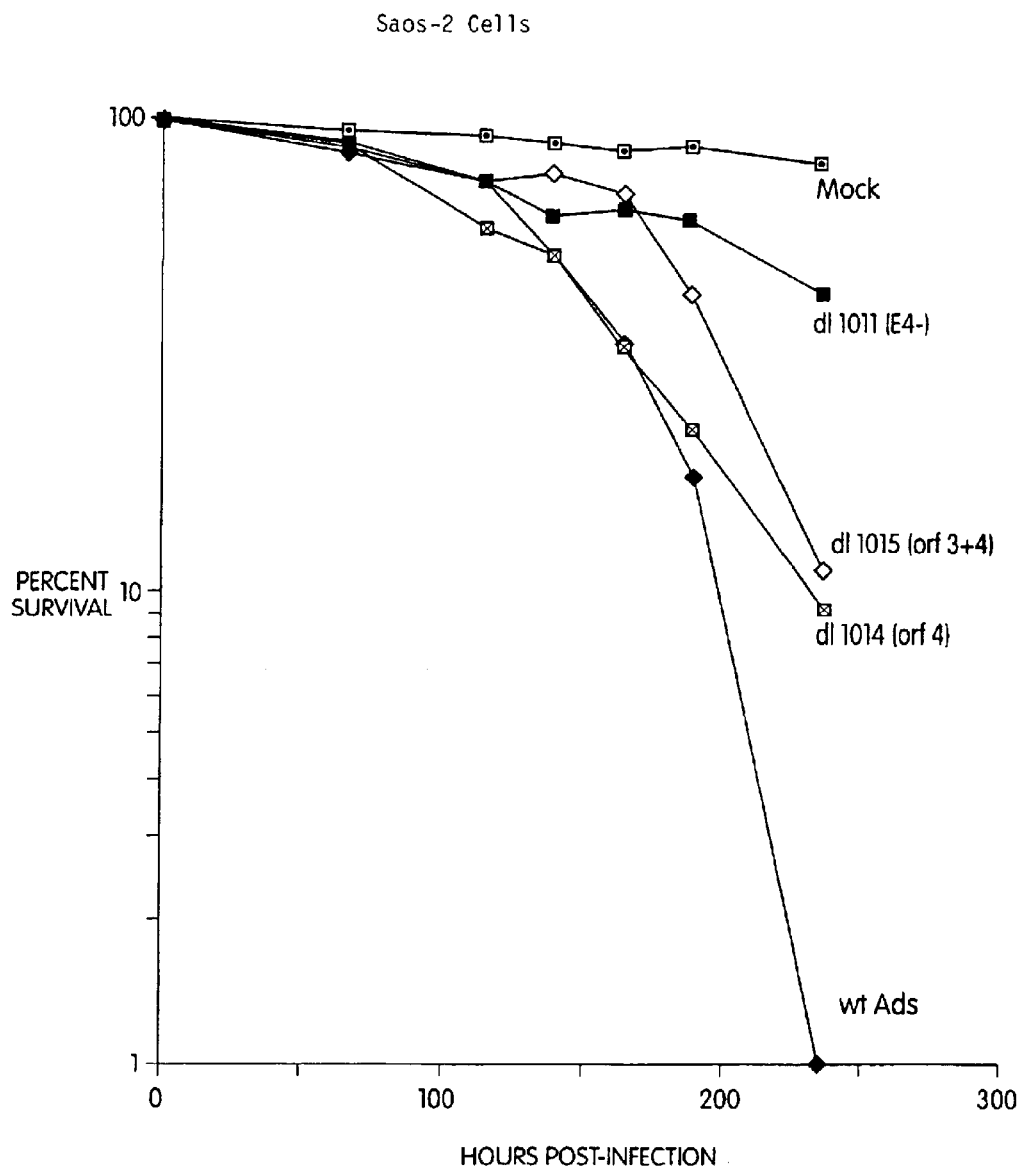
FIG. 12 is a graph of the Trypan Blue™ exclusion analysis showing the role of E4orf4 in p53-independent cell killing (in p53-null Saos-2 cells)

To identify which E4 product is responsible for induction of E1A-dependent p53-independent apoptosis, p53-null mouse 10(1) cells were infected with wt Ad5 or with mutants carrying deletions in various portions of the E4 region (see FIG. 10). Saos-2 cells were infected with wt Ad5, Ad5 mutants, or were mock-infected, and cell viability assays using Trypan Blue™ were conducted at various times after infection. Results have been presented as the logarithm of the % viable cells, and symbols are as indicated in FIGS. 11 and 12. FIG. 11 shows that Saos-2 cells infected by the wt virus began to die by about 125 hours following infection, and death was almost complete by 240 hours, as judged by Trypan Blue™ exclusion by living cells. Little cell death was observed in mock-infected cultures or in cultures infected by mutants dl1019 and dl1011, which lack the entire E4 region. Cell death similar to that found with wt was observed with E4 mutants dl1013 which expresses E4orf6 and E4orf4, whereas little death occurred with mutant dl1010 which expresses all E4 products except E4orf6 (FIG. 11). These results indicated that cell death occurred only when the E4orf6 protein was expressed and did not take place during the course of the experiment in its absence. Thus, it is clear that expression of the E4orf6 protein is essential for the p53-independent apoptosis induced by the 289R E1A product.

Studies with dl1013 left open the possibility that E4orf4 may also be involved in p53-apoptosis induced by the 389R E1A product, so additional mutants were tested. Further Trypan Blue™ exclusion experiments on Saos-2 cells following infection with mutants dl1014, which expresses E4orf4 only, dl1015, which expresses E4orf4 and E4orf3, dl1011, which expresses no E4 products, as well as mock-infected cells, were conducted. FIG. 12 shows that indeed mutant dl1014 which produces E4orf4 but no other E4 product killed quite effectively. These results indicated that expression of E4orf4 alone induced cell death. Mutant dl1015 which produces only E4orf4 and E4orf3 killed reproducibly less well than dl1014, suggesting that the E4orf3 protein may lessen the toxic effects of E4orf4.

Thus, FIGS. 11 and 12 demonstrate that adenovirus Ad5 produces two proteins, E4orf6 and E4orf4, that each plays a role in the induction of p53-independent apoptosis. This conclusion was confirmed in a second type of experiment in which either E4orf4 or E4orf6 was expressed alone in the absence of other viral proteins using transient transfection with E4orf4 or E4orf6 plasmid DNA in combination with a reporter plasmid encoding luciferase in p53 expressing or p53-null transformed cells.

Figure 13A:
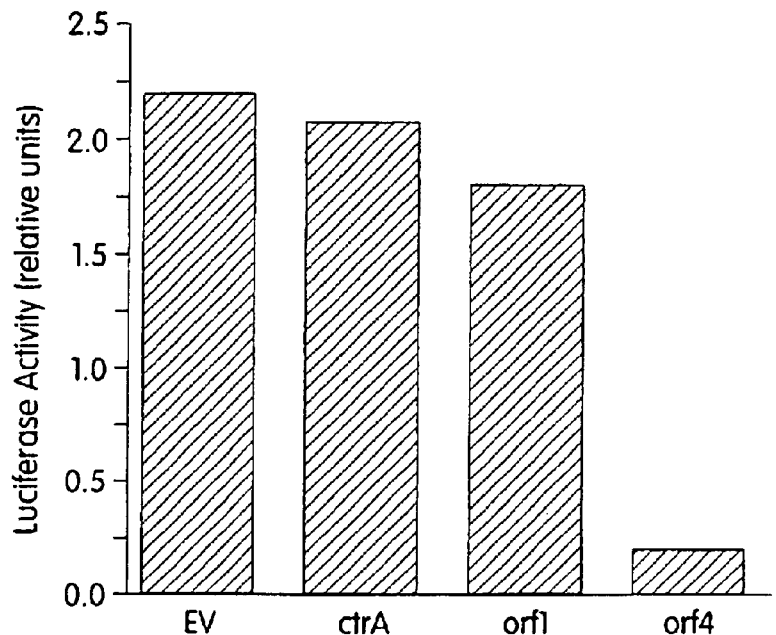
FIGS. 13A and 13B are graphs showing that E4orf4 or E4orf6, when expressed by transient transfection of an E4orf4 or an E4orf6-encoding plasmid, induces cytotoxicity in p53-null cells, as judged by the low expression of a co-transfected reporter plasmid encoding luciferase, relative to non-cytotoxic inducing control plasmids encoding E4orf1, E4orf3, and crmA.
Figure 13B:
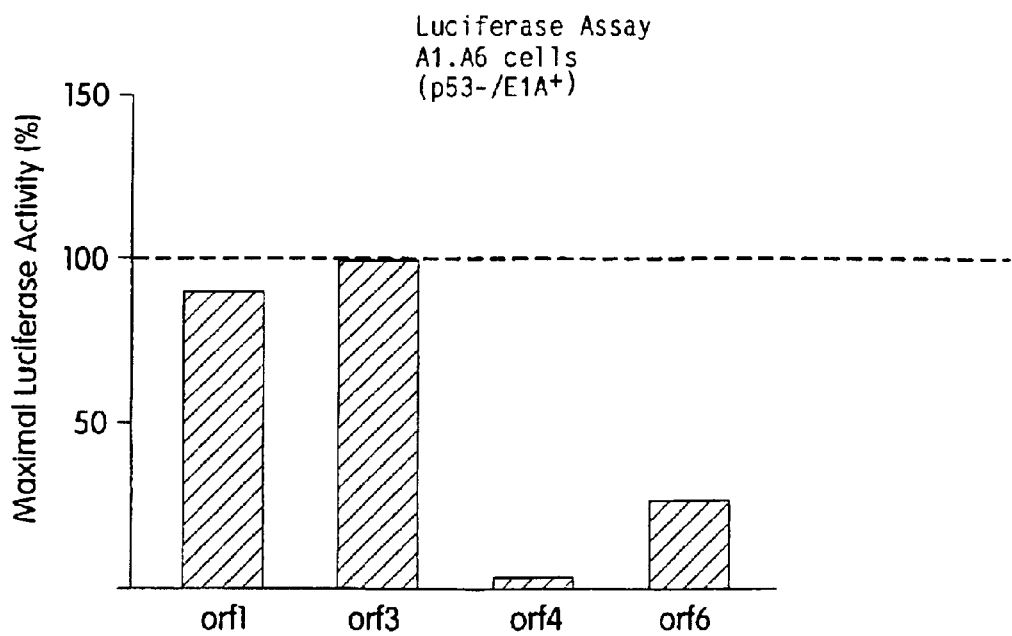
Figure 14:
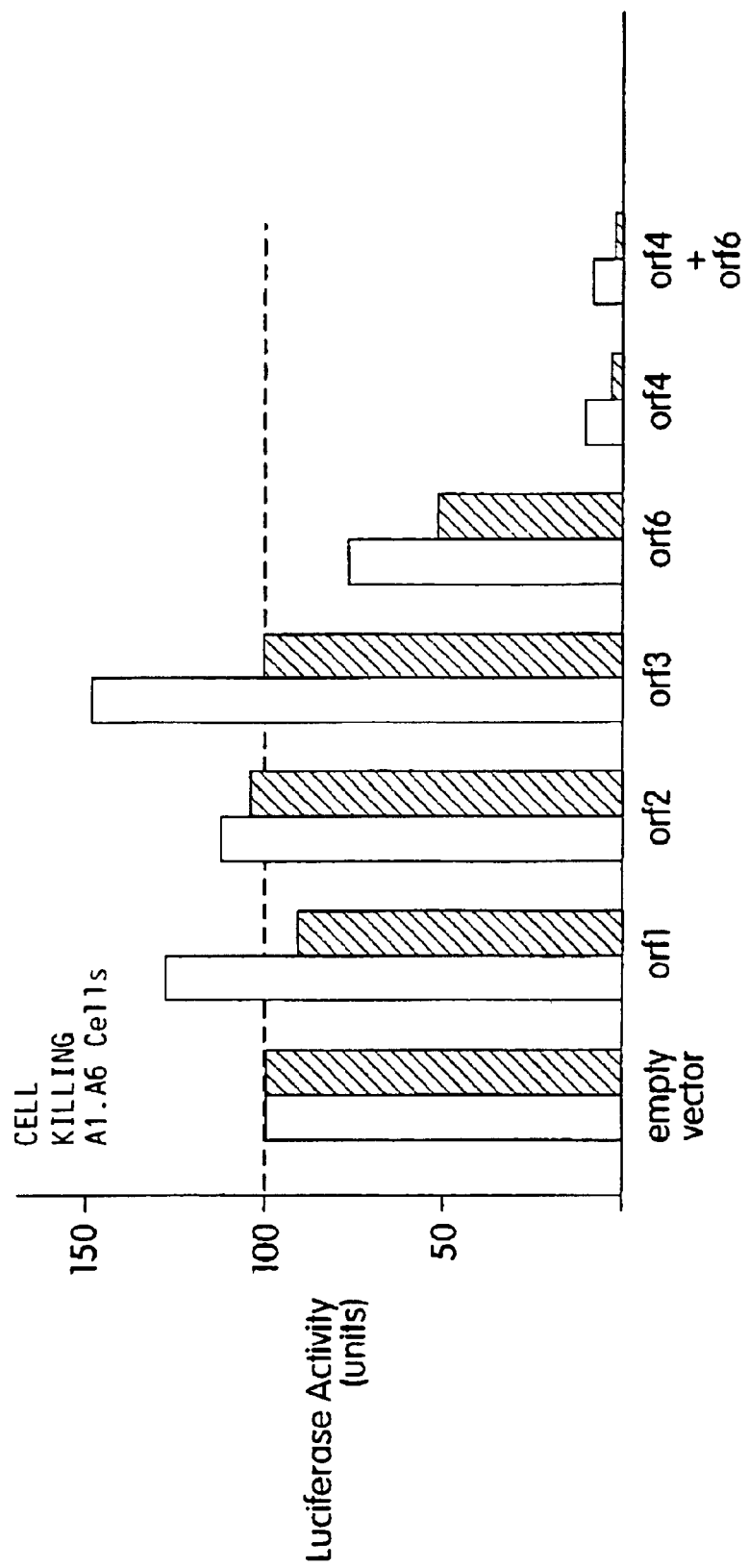
FIG. 14 is a graph showing that E4orf4 and E4orf6, when expressed individually or together with luciferase by transient transfection of an E4orf4- or an E4orf6encoding plasmid induces cytotoxicity in p53-null cells, as judged by the low expression of a co-transfected reporter plasmid encoding luciferase, relative to non-cytotoxic inducing control plasmids encoding E4orf1, E4orf2, and E4orf3. Two concentrations of the E4orf plasmid DNAs were used: black bars indicate 2.5 µg; cross-hatched bars indicate 5 µg.

1A.A3 and A1.A6 cells, which lack p53 but express the E1A oncogene constitutively, were co-transfected using the calcium phosphate method with a cDNA plasmid encoding luciferase operably linked to the RSV promoter (pRSV-luciferase) and either cDNA plasmids expressing various E4 products or crmA operably linked to the CMV promoter. These constructs were generated by subcloning the cDNA sequences encoding these protein products into the pCDNA3.1 expression plasmid commercially available from Invitrogen. Forty-eight hours following transfection, cells were lysed and luciferase activity was measured on a luiminometer using the methods and reagents of the luciferase assay kit commercially available from Promega. The luciferase activity in FIG. 13A is represented in units of activity, whereas the luciferase activity in FIG. 13B is represented a percentage of the maximal luciferase activity observed in cells co-transfected with luciferase- and E4orf3-encoding plasmids. FIGS. 13A and 13B show that transfection by empty vector (EV), or cDNAs expressing E4orf1, E4orf3, or CrmA resulted in high levels of luciferase activity, indicating that cell viability was unaffected. However FIGS. 13A and 13B show that luciferase activity was partially reduced by expression of E4orf6 (FIG. 13B), and greatly reduced by that of E4orf4 (FIGS. 13A and 13B). Co-expression of both of the E4 death proteins resulted in even greater cell killing, as is shown in FIG. 14. These results provided independent evidence of the ability of both of these proteins to kill p53-null transformed cells, while at the same time demonstrating the inability of E4orf1 and E4orf3 to kill these cells. Similar killing assays have yielded comparable results in p53-positive transformed cell lines and some immortalized rapidly-growing cells. In all assays of this type, E4orf4 was found to induce higher levels of killing than E4orf6. However, it is difficult to predict whether or not the higher level of killing observed with E4orf4 is either as desirable or as specific as that obtained with E4orf6. Nonetheless, these results indicated that both E4orf4 and E4orf6 have the potential to kill rapidly growing transformed cells. Furthermore, as discussed herein, because such killing did not occur in normal cells infected by mutants in which E1A products were defective in their ability to induce unscheduled DNA synthesis and cell transformation, killing is limited to cancer cells, leaving normal cell populations relatively unaffected.

Adenovirus E1A products induce DNA degradation, rapid cell death and other hallmarks of apoptosis when expressed in the absence of E1B products, whose major role in lytic infection and transformation is to suppress E1A toxicity. Both the 289R and 243R E1A proteins are able to induce apoptosis through p53-dependent pathways.

E1A proteins also induce apoptosis in cells lacking p53 (Teodoro, J. G. et al., 1995, Oncogene 11: 467–474). We found that this p53-independent apoptosis was elicited only by the 289R E1A protein, and our results suggested that expression of one or more additional early viral genes regulated by E1A-289R was required for this apoptosis. The experiments described herein indicated that the E1B-55 kDa protein was unable to block this effect, but both the E1B-19 kDa product and the cellular suppressor of apoptosis, Bcl-2, significantly inhibited this response.

The major goal of the work leading to this invention was to identify which early viral transcription units were required to induce cell death in the absence of p53. Results obtained with E1A mutants clearly indicated that the CR3 is important in the ability of the E1A 289R product to induce p53-independent apoptosis. Furthermore, CR3-mediated transactivation activity appeared to be required, as several point mutants in CR3 which were known to eliminate transactivation of target genes were defective for induction of DNA degradation and cell killing. Of great interest were results obtained with mutants with defects outside CR3. Mutant dl1108, which lacks the core binding site for pRB and related proteins, induced p53-independent apoptosis like wt. However, mutant dl1101, which binds pRB at reasonably normal levels but fails to bind the p300 transcriptional modulator, was totally defective in its ability to induce p53-independent apoptosis. These results suggest that interactions between p300 and 289 R are essential to institute cell death pathways. Another possibility was offered by results obtained with two additional mutants with defects in the AR1 and AR2 regions encoded by the second exon of the 13S E1A mRNA. The AR1-defective mutant was unable to induce p53-independent apoptosis, and the mutant lacking AR2 was also somewhat impaired its ability to induce p53-independent apoptosis. These results corresponded exactly to the relative abilities of these mutant E1A molecules to transactivate the E4 promoter. We also found that dl1101 was partially defective for transactivation of E4, thus indicating that not only are E4 products involved in induction of cell death, but also that interactions of 289R with p300 may reflect more a requirement for transactivation of E4 transcription than a direct role in apoptosis.

Early regions E2, E3 and E4 encode a variety of products which could play some role in cell death. E2 proteins are largely involved in viral DNA synthesis. However, it is unlikely that any E2 proteins play an essential role in cell death. First, E2 transcription requires not only CR3, but also the formation of complexes with pRB which result in the activation of the E2F family of transcription factors and E2 gene expression. Our results clearly indicated that complex formation with pRB was not essential for apoptosis. Second, the adenovirus vector AdRSVβgal.11 contained a wt E2 region and yet was defective for induction of p53-dependent apoptosis in E1A-expressing cells. The E3 region encodes several proteins which affect virus-host interactions, however, the adenovirus vector Ad5dl70-8, which lacks expression of E1A, E1B, and E3, was fully capable of inducing apoptosis in E1A expressing p53-deficient cells. The pattern of apoptosis we observed with E1A mutants suggested that the early viral proteins associated with cell death were encoded by E4. Direct evidence that an E4 protein was responsible was obtained from experiments in which the pattern of death was observed in p53-null Saos-2 cells infected by wt Ad5 or a mutant defective in E4 expression. Because E1B products were expressed by these viruses, cell death occurred only at late times, but the observation that E4 mutant-infected cells displayed considerably retarded death clearly implicated an E4 product in the death process. Final confirmation came from the results of experiments with the ADRSVβgal.11 adenovirus vector which demonstrated that this viral vector was defective for cell killing. This virus was unable to induce DNA degradation or cell killing in p53-deficient cells expressing E1A.

Hence, we have shown that either of the E4 death proteins, E4orf6 or E4orf4, is responsible for the ultimate death of human cells following productive infection by adenoviruses. Cell death could be induced early after infection following expression of E1A proteins, however, p53-dependent apoptosis, which is induced directly by E1A, is blocked by expression of both the 55 kDa and 19 kDa E1B proteins. Following expression of E4orf4 or E4orf6 proteins, infected cells would die by p53-independent apoptosis were it not for the E1B-19 kDa product which blocks cell death until late in infection. Cell death may eventually occur because the levels of the E4orf4 or E4orf6 become too elevated for suppression by E1B-19K.

The E4orf4 and E4orf6 proteins are of use in killing cells that accumulate in several disease states, including some auto-immune disorders and cancer. Such cells fail to die by apoptosis and, at least in many cancers, one reason is because many cancer cells lack or express a mutant form of p53. These cells would, however, be susceptible to killing by the E4orf4 and E4orf6 proteins.

E4orf6 is known to form complexes with E1B-55K. These complexes regulate late transport and stability of viral mRNAs and play a role in the late shut-off of host cell metabolism. We have found that E4orf6 and E1B-55K block the accumulation of p53, and that all three of these proteins interact directly. E4orf4 has been found to bind to and activate protein phosphates 2A (PP2A), which results in decreased phosphorylation of both E1A-289R and some transcription factors (Muller, U. et al., 1992, J. Viol. 66: 5867–5878; Bondesson, M. et al., 1996, J. Virol. 70: 3844–3851). We have also found that decreased phosphorylation of E1A probably results from the inactivation by PP2A of MAP kinase which acts on sites in CR3 required for efficient transactivation of E4.

The present invention allows the utilization of E4orf4 and E4orf6 adenovirus death proteins as therapeutic agents with the ability to induce apoptosis in tumor cells for the treatment of human cancers, including p53-null tumors, since these proteins are able to kill tumor cells whether p53 is present or not. Furthermore, because normal cells lack inappropriate growth signals such as those delivered by E1A or activated cellular oncogenes, these E4 death proteins have little effect on normal tissues.

VIII. Additional Cell Killing Assays

It will be understood by the skilled artisan that cell killing assays in addition to the assays already described herein may be utilized for the identification of regions of E4orf4 and E4orf6 important for cell killing, as well as the identification of other viral death proteins and reagents. Additional killing assays may be developed in which the effects of the individual viral proteins can be measured in the entire cell population. Such assays are especially critical in determining the selectivity of killing by these agents. New killing assays allow a meaningful analysis of the killing potential of the E4 death proteins, fragments thereof, and other viral death proteins, and may include: virus infection assays utilizing E4/E1B Ad5 double mutants, colony formation assays using drug selection, cell killing assays using adenovirus vectors expressing E4orf4 and E4orf6, cell killing assays using retroviral vectors expressing E4orf4 and E4orf6, and the generation of cell lines expressing E4orf4 and E4orf6 under an inducible promoter (e.g., tetracyline).

E4/E1B Double Mutants

E4 mutations may be introduced into the mutant pm 1716/2072, which is defective in production of the E1B-19K protein (McLorie, W. et al., supra). Such mutants are defective for protection against p53-independent apoptosis, but the absence of 19K alone does not greatly affect viral yields. In addition, the existence of E1B-55K enhances efficient viral replication and protects against E1A-induced p53-dependent apoptosis. Thus, such E4 mutants can be grown efficiently in W162 cells, a monkey cell line which expresses the entire E4 region (Bridge, E. et al., supra). Viral mutants are generated by BamH1 restriction endonuclease cleavage of pm1716/2072 and the series of E4 mutants, which generates DNA fragments of about 14 and 21 kDa. Mixing and re-ligation of these fragments will yield recombinant viruses which are defective in both E1B-19K and E4. Such viruses can then be used in the rapid cell death assays described herein to confirm the killing efficiency of the various E4 products and to relate it to results obtained in longer term infection/killing assays. With this approach, killing of the entire cell population can be assessed rapidly.

Colony Formation Assays

A second approach is to determine the ability of the E4 death proteins to prevent cell colony formation. If the E4 proteins induce cell death effectively, colony formation should be reduced because the cells are killed. Thus, DNA constructs were made in which E4orf4 and E4orf6 were introduced into an expression plasmid (e.g., pCDNA3.1) carrying a drug selectable marker (e.g., neo), as described herein. Following transfection, the number of colonies formed in the presence of G418 will be counted. With this system, the E4 proteins can be assessed in the absence of other viral products and the killing process relies on inhibition of cell growth.

Adenovirus Vectors

The E4orf4 and E4orf6 proteins may be introduced into an adenovirus gene therapy vector, such as Ad5dl70-8 (Bacchetti, S. et al., 1993, Inter. J. Oncol. 3: 781–788). We have generated a number of such vectors using simple cloning methods. We also envision the use of adenovirus vectors in which the E4 death proteins are expressed via an inducible promoter such as tetracycline. Such vectors could be produced using standard recombinant DNA techniques. With this approach, all cells in the population can be induced to express the E4 death proteins.

Retroviral Vectors

A preferred approach is to introduce the E4 death proteins into the mouse retroviral vector pBABE (Morgenstern and Land, 1990, Nucl. Acid Res. 18: 3587–3596) which will express high levels from the viral LTR. Such vectors also contain drug selection markers which are useful for additional studies. The E4 death protein cDNAs are cloned into pBABE and viruses prepared in cells which contain the mouse virus receptor. Virus is then harvested from the cell supernatant and used to infect mouse cells or human lines expressing the virus receptor. With this approach, the death proteins can be introduced into all cells in the culture, and expression from the vector is prolonged and would detect killing functions that require extended time periods. In addition, pBABE vectors in which the inserted cDNA is driven by an inducible promoter (e.g., tetracycline) may be constructed by standard recombinant DNA techniques. Utilization of such a recombinant virus allows the simultaneous expression of inserted DNA.

Cell Lines Expressing E4 Death Proteins

A number of human and rodent cell lines are established which express the E4 death proteins under an inducible promoter, namely tetracycline. In one example, tet promoters exist which are activated by addition of tetracyline. These promoters can be PCR amplified and inserted into the pCDNA vectors expressing the E4orf4 and E4orf6 proteins described herein. These plasmids can then be transfected into desired cell lines, followed by incubation of the transfected cell lines in G418 containing growth media. Cells resistant to G418 may then be cloned by limiting dilution, and individual clones induced by the addition of tetracycline. Expression level of individual clones may then be assessed utilizing antisera specific for E4orf4 and E4orf6. The advantage of this inducible expression system is that all cells can be exposed to the death proteins simultaneously following induction.

All cell killing assays described above may be carried out with E4orf4 and E4orf6 either alone or in combination with each other or additional proteins, including other viral products, activated cellular or viral oncogenes, or suppressors of apoptosis.

IX. Selectivity of Cell Killing

An important feature of an effective anti-cancer agent is the selectivity of cell killing. Clearly many toxic agents exist, but a key property is the ability to kill cancer cells selectively and leave normal tissues relatively unaffected. One approach is to target toxic compounds selectively to cancer cells though the use of immunological or biochemical targeting molecules. This approach has been attempted many times with limited success (Hall, S. S., 1995, Science 270:915–916). The present invention describes an approach in which an agent which is biologically active only in cancer cells (e.g., E4orf4 or E4orf6, or a combination thereof) is used to selectively induce death in cancer cells. The E4orf4 and E4orf6 proteins only kill cells which express an inappropriate growth signal, such as one provided in cancer cells by activated oncogenes or perhaps by inactivated tumor suppressors. Thus, introduction of the E4 death proteins into normal cells has little effect, whereas in cancer cells which possess signals for unregulated cell growth, these proteins are lethal.

We have shown in the present invention that the E4 death proteins (E4orf4 and E4orf6) are selective. Cells infected with a mutant Ad5 which expressed a defective E1A product lacking the ability to bind to p300/CBP and thus unable to provide a signal for unregulated DNA synthesis and cell growth, were not killed by the E4 death proteins. This result allowed the conclusion that cells must receive a signal for unregulated DNA synthesis and cell growth to be receptive to E4 killing. Two other kinds of experiments supported this conclusion. In cotransfection luciferase assays as described herein, whereas several human and monkey cell lines which exhibit 'normal' growth properties appeared to be relatively unaffected by transfection with cDNAs expressing E4orf4 and Erorf6 and exhibited high levels of luciferase activity, Ad5-transformed tumorigenic human 293 cells expressed diminished luciferase activity when co-transfected with E4orf4 and E4orf6. As was the case in FIGS. 13B and 14, the killing potential in these assays was again significantly greater with E4orf4 than with E4orf6.

Likewise, colony inhibition assays were conducted in which cells were co-transfected with cDNAs expressing one of the E4 death proteins or a control, as well as a second construct encoding either the neo or puromycin drug selectable marker. In human 293 and Saos-2 osterosarcoma-derived human cells and in E1A-transformed mouse 1A.A6 cells, co-transfection with E4orf4 cDNA reduced colony formation by about 80% relative to a control vector lacking the E4orf4 coding sequence. The reduction was less with E4orf6: about 30% in the case of Saos-2 cells. These colony inhibition approach experiments further demonstrated that transformed cells were more susceptible to E4orf4- or E4orf6-induced killing than non-transformed cells.

X. Establishment of Killing Specificity for Cancer Cells

Using the killing assays and constructs described herein, we are able to test the specificity of killing of the E4orf4 and E4orf6 death proteins and determine the degree of cell killing in normal and transformed cancer cells. In the case of rodent cells, normal cells may include primary kidney epithelial cells from normal rats or from normal or p53-null mice. A variety of transformed or tumor derived rodent cells may also be tested. In the case of adenovirus or retrovirus experiments, studies are conducted on density-inhibited or serum-deprived rodent cells to establish if cell growth rate affects killing. In the case of human cells, similar studies may be conducted on a variety of "normal" human cell lines, including MRC5, IMR90, WI-38, and on a variety of transformed or tumor derived cells, especially those which have been characterized for p53 expression. The number of such lines may be extended by appraising p53 expression with, for example, Western blotting analysis techniques using commercially available p53-specific antibodies (from, e.g., Santa Cruz Biotechnology, Inc.), to include a wide variety of human tumors in order to establish the range of cancer types killed by the E4 death proteins. These various cell lines are commercially available from the ATCC (Rockville, Md.). These studies provide clear information on the specificity of killing for neoplastic cells.

A particularly important variation on these experiments is to co-express, in normal cells, a variety of activated human oncogenes in concert with the E4 death proteins. Such studies directly test the degree of enhanced cell killing in the presence of growth altering oncogene products.

XI. Identification of the Minimal Killing Domains of the E4 Death Proteins

To selectively kill cancer cells, it is desirable to localize the minimal killing domains of the E4orf4 and E4orf6 proteins. The minimal killing domains are likely located within the known active sites of these proteins, although there may be, as yet, unknown functions for these proteins. Peptide fragments encompassing domains with or without known function of the E4orf4 and E4orf6 proteins are generated and assessed for cell killing capabilities.

The only known function of E4orf4 is to bind to and activate PP2A (Kleinberger and Shenk, 1993, J. Virol. 67: 7556–7560). Such activation may result in the dephosphorylation of components of the cell death pathway, resulting in induction of apoptosis. E4orf6 is also known to form complexes with at least two proteins, p53 and E1B-55K, and to carry out a number of different functions involved in the viral infectious cycle (Samow, P. et al., 1984, J. of Virol. 49: 692–700; Dobner, T. et al., 1996, Science 272:1470–1473).

A series of mutants are constructed to map the regions within E4orf4 and E4orf6 which are responsible for induction of p53-independent apoptosis. Deletion mutants are generated which eliminate increasing stretches of the N- and C-termini of these proteins. In addition, in-frame deletion of selected internal hydrophilic regions are created and point mutants at critical conserved residues are generated. Methods for the generation of such mutants are well known in the art (see, for example, Ausubel, F. et al., supra). For example, a deletion mutant eliminating the N-terminus of the E4orf4 proteins may be generated by PCR amplifying the E4orf4 cDNA containing pCDNA3.1 vector described herein with primers corresponding to the desired C-terminal portion of the protein. Preferably, the PCR primers include restriction endonuclease recognition sequences at their 5' ends which facilitate insertion of the PCR product into an expression cloning vector (e.g., pCDNA3.1). The resulting plasmid may then be subjected to DNA sequence analysis. Expression may be assessed by transfection of the fragment-encoding plasmid into a eukaryotic cell line (e.g., COS cells), followed by detection of the desired fragment by Western blotting analysis of transfected cell lysates with anti-E4orf4 antibodies.

Introduction of mutants into, for example, pBABE retroviral vectors or application of standard luciferase assays allow rapid determination of the killing potential of the fragments in cells, such as those described herein, which are known to be readily killed by these proteins. Once the killing regions are identified they are fine mapped through the generation of more specific in-frame deletions or point mutations. Protocols for these techniques are well known in the art of molecular biology. In addition, various DNA mutation kits are commercially available, such as Clontech's Transformer™ Site-Directed Mutagenesis Kit. The identification of such killing domains also provides important information on the mechanism of killing as sequences may be compared with PP2A binding, in the case of E4orf4, or one of the several known biological activities of E4orf6.

Other preferred fragments and mutants thereof are those which include conservative amino acid substitutions. Preferable fragments include fragments, or mutants thereof, which increase the biological activity (i.e., cell killing activity) or stability (i.e., half-life) of the E4 death proteins.

XII. Generation of Anti-E4orf4 and Anti-E4orf6 Antibodies

Once introduced into a cell, determination of expression of E4orf4 or E4orf6, or fragments or mutants thereof is desirable. One method for the determination of expression is the utilization of antibodies specific toward these proteins. High titre antisera directed against both the—and C-termini of E4orf6 has been generated, and similar sera directed against the—and C-termini of E4orf4 are also produced. These antisera are produced using both fusion products and synthetic peptides corresponding to the E4orf4 and E4orf6 death proteins as immunizing antigens according to standard protocols (see, e.g., Ausubel, F. et al., supra). Specificity and titre of antisera may be assessed by standard molecular biology techniques such as Western blotting analysis, immunoprecipitation, and ELISA.

XIII. Identification and Generation of Peptide Mimetics Corresponding to the E4orf4 and E4orf6 Killing Domains One efficient method to treat cancer patients with the E4 death proteins' functions is to generate mimetics which possess the killing effects of the E4orf4 and E4orf6 proteins. The mechanism of toxicity of neither protein appears to contain enzymatic activity, and they function through complex formation with cellular proteins.

Once the killing domains have been mapped, synthetic peptides corresponding to these regions may purchased from commercially available sources (such as the Sheldon Biotechnology Centre, McGill University, Montreal, Que., Canada), and tested for toxicity in the cell killing assays described herein. Such peptides may be taken up directly by cells in culture or delivered to the cells by a variety of methods, including lipid vesicles or electroporation. In addition, nucleic acid sequences encoding these peptides may be subcloned into the cloning site of an expression cloning vector (e.g., pCDNA3.1) and the plasmid DNA introduced to the cell of interest by various transfection methods known in the art (e.g., electroporation, DEAE-dextran, calcium phosphate). DNA encoding peptides corresponding to the killing domains of E4orf4 and E4orf6 may also be incorporated into coding sequences of fusion proteins and the mimetic delivered by transfection of the fusion protein encoding expression vector or fusion protein encoding viral vectors.

It will be understood that peptide mimetics of E4orf4 and E4orf6, or DNA encoding these peptides, may be used in concert. For example, two or more different E4orf4 peptides which correspond to different regions of the E4orf4 killing domain may be introduced into the same population of cells. E4orf4 peptide mimetic(s) may also be introduced with one or more peptide mimetics corresponding to the E4orf6 killing domain into the same population of cells.

Peptides, or combinations thereof, may be screened for efficacy and effective dose requirements using the various cell killing assays described herein. For example, various concentrations of peptide may be introduced with the luciferase-expressing plasmid (pRSV-luciferase) described herein into 1A.A3 cells. Forty-eight hours following introduction, cells are lysed and luciferase activity assessed using the Promega luciferase assay kit (Catalog #E1500). A cell killing peptide will induce cell killing (i.e., reduce luciferase activity) in 1A.A3 cells as compared to 1A.A3 cells transfected with a non-death inducing control (e.g., crmA).

DNA encoding potential peptide mimetics of E4 death proteins may also be identified by hybridization of the DNA to the nucleotide sequences encoding E4orf6 (SEQ ID NO.: 1) and E4orf4 (SEQ ID NO.: 3), provided on FIGS. 15 and 16, respectively. In one particular example of this approach, DNAs may be identified by an ability to hybridize to the adenovirus nucleotide sequences under high stringency conditions. High stringency conditions may include hybridization at about 40° C. in about 2×SSC and 1% SDS, followed by a first wash at about 65° C. in about 2×SSC and 1% SDS, and a second wash at about 65° C. in about 1×SSC. Other hybridization stringency conditions, both high and low, are defined in the art (see, for example, Sambrook, Fritsch and Maniatis, *Molecular Cloning: A Laboratory Manual* (2d ed.), CSH Press, 1989, or Ausubel, F. et al., supra).

Once identified, a DNA which hybridizes to the nucleotide sequences encoding E4orf4 or E4orf6 may used to generate a polypeptide product by standard techniques. For example, the DNA may be subcloned into pCDNA3.1 and the resulting plasmid transfected into, for example, COS cells (commercially available from the ATCC), to produce recombinant polypeptide). This polypeptide product may then be screened for E4orf4 or E4orf6 biological activity using the various cell death assays described herein.

XIV. Production of Non-Peptide Mimetics

The identification of minimal peptide killing sequences allows the generation of non-peptidic mimetics. Techniques for generating such non-peptidic mimetics of the killing domains of E4orf4 and E4orf6 are standard chemistry techniques and well known to one skilled in the art of combinatorial chemistry. The efficacies of these non-peptide mimetics may be assayed similarly to peptide mimetics of E4orf4 and E4orf6 killing domains.

XV. Screens for Additional Reagents Which Mimic E4 Death Proteins

It is understood that different compounds may have the same mechanism of action without concomitant similarity in size and/or structure. Accordingly, although peptide and non-peptide mimetics based upon the killing domains of E4orf4 and E4orf6 are likely to induce an E4 death protein-like apoptosis in transformed cells, non-mimetic reagents may also have this capability. Utilizing the cell death assays described herein, such reagents may be identified.

In one approach, 1A.A3 cells stably expressing a detectable protein (e.g., green fluorescent protein (GFP)) may be generated by transfecting 1A.A3 cells with pCDNA3.1 (Invitrogen) encoding GFP and then culturing the transfected cells in the presence of G418. These GFP-expressing 1A.A3 cells may then be contacted with a reagent or combination thereof being tested for an ability to induce an E4 death protein cell death. Following contact, the cells may be analysed by flow cytometry for living cells expressing GFP. A compound or reagent which induces an E4orf4 or E4orf6-like apoptosis will reduce the number of living cells expressing GFP as compared to a cell not contacted. Living cells versus non-living cells may be differentiated by size (i.e., side scatter and forward scatter profiles on a flow cytometer), or by staining with Propidium Iodide.

In another flow cytometry-based screen, reagent-contacted and non-contacted cells may be stained with Annexin V coupled to FITC (Endogen), followed by flow cytometry analysis. This type of apoptosis assay is based upon the presence of phosphatidyl-serine on the inner leaflet of the cell membrane. While a healthy cell does not bear phosphatidyl serine on its cell surface, a cell undergoing apoptosis does, as part of the apoptotic process. Annexin V binds with high affinity to phosphatidyl-serine residues, and coupling of Annexin V to FITC allows detection of apoptotic cells by flow cytometry.

It is understood that cell death analyses need not be by flow cytometry. For example, DNA fragmentation may be used as a method to detect apoptotic cells.

In a preferred embodiment, screens for reagents which induce an E4 death protein-like cell death are rapid and high through-put. For example, GFP-expressing 1A.A3 cells may be cultured in a multi-well (i.e., a 96 well microtiter) plate. Following contact with reagents being screened for an ability to induce an E4 death protein-like cell death wherein a different reagent or combination thereof is added per well of cells, the plate may then be subjected to analysis on a 96 well plate reader for the presence of GFP. A well with reduced GFP expression compared to a control untreated well indicates a compound with an ability to induce an E4 death protein-like cell death.

XVI. Apoptosis-inducing Reagents Which Activate Protein Phosphates 2A (PP2A)

Given the well characterized function of E4orf4 in binding to and activating PP2A (Kleinberger and Shenk, 1993, J. Virol. 67: 7556–7560), reagents which activate PP2A are useful in inducing cell death in transformed cells. Reagents which activate PP2A are readily identified using commercially available reagents. In one approach, cells, for example, human Saos-2 cells, are contacted with reagents being screened for an ability to activate PP2A. Following contact, cells are lysed, and PP2A is immunoprecipitated with commercially available anti-human PP2A antibodies (from, e.g., Upstate Biotechnology, Inc.). The PP2A immunoprecipitates may then be subjected to any of a number of standard phosphates assays known in the art. An increase in the activity of PP2A as compared to PP2A isolated from untreated cells indicates a compound which activates PP2A and is able to induce E4orf4-like cell death. These compounds may be subjected to a secondary cell killing assay screen, as described herein.

XVII. Identification of Other Viral Death Proteins

In addition to the Ad5 E4orf4 and E4orf6 death proteins, proteins from other viruses also induce apoptosis. Thus, such proteins may also prove to have efficient anti-cancer activities which may be specific or wide range. Other adenovirus proteins, or proteins from other viruses, such as the NS protein of the B-19 human parvovirus, which is known to control replication and cell killing only in rapidly dividing cells (Ozawa, K. et al., 1988, J. of Virol. 62:2884–2889), may be assayed in the cell killing assays described herein for a specific transformed cell killing ability.

XVIII. Analysis of E4 Death Proteins of Additional Human Adenoviruses

The present invention allows the analysis of the E4orf4 and E4orf6 proteins of selected adenoviruses among the more than 40 human serotypes for toxicity by the methods described herein. Different serotypes maintain a degree of sequence homology but also possess varying and interesting differences which may result in proteins of potentially differing potency or specificity. The corresponding E4 cDNAs from additional adenovirus serotypes are cloned by a variety of approaches well known in the art of molecular biology. These proteins are then assessed for an ability to induce cell death in transformed cell lines using the assays described herein.

XIX. Adenovirus E4 Death Proteins to Treat Cancer

The present invention allows the use of adenovirus E4 death proteins in the treatment of cancers, especially those cancers which are p53-negative and which are difficult to eliminate by existing therapies. This invention allows the development of non-peptidic mimetics which may be used as reagents to treat cancers without the problem of specific targeting and the complication of toxicity to normal tissues. Converting highly evolved viral functions into chemotherapeutic agents is novel, and has great potential for this and other disease treatment regimes.

XX. Administration of E4 Death Proteins and Reagents Thereof

An adenovirus E4orf4 or E4orf6 protein, nucleic acid, or mimetic reagent may be administered within a pharmaceutically-acceptable diluent, carrier, or excipient, in unit dosage form. Conventional pharmaceutical practice may be employed to provide suitable formulations or compositions to administer E4orf4 and/or E4orf6 proteins or E4orf4 or E4orf6-mimicking reagents (e.g., peptide or non-peptide mimetics) to patients suffering from a disease (e.g., cancer) that is caused by reduced apoptosis. Administration may begin before the patient is symptomatic. Any appropriate route of administration may be employed, for example, administration may be parenteral, intravenous, intra-arterial, subcutaneous, intramuscular, intracranial, intraorbital, ophthalmic, intraventricular, intracapsular, intraspinal, intracistemal, intraperitoneal, intranasal, aerosol, by suppositories, or oral administration. Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in *Remington's Pharmaceutical Sciences* (18$^{th}$ edition), ed. A. Gennaro, 1990, Mack Publishing Company, Easton, Pa. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for E4orf4 or E4orf6 death proteins and mimetics thereof include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

If desired, treatment with an E4orf4 or E4orf6 protein, gene, or mimetic reagent may be combined with more traditional therapies for the disease such as surgery, steroid therapy, or chemotherapy for autoimmune disease; antiviral therapy for AIDS; and chemotherapy for cancer.

Dosage requirements for the administration of the E4 death proteins, or mimetics thereof, may be initially determined in the cell killing assays described herein (e.g., the luciferase assay) on cultured cells. It is understood that cells of different origin may be assessed by this method for dosage requirements. For example, a human p53-null carcinoma cell line may be acquired from the ATCC and used to determine the preferred dosages to treat patients suffering from cancers of this origin. It is understood, however, that further dosage requirements for treatment of patients may be assessed in vivo in each individual and may vary based upon body mass and tumor size.

XXI. Therapies

Therapies may be designed to induce E4 death protein-mediated apoptosis in transformed cells. Apoptosis-inducing E4 death protein reagents may include, without limitation, E4orf4 and E4orf6 full length proteins, polypeptide fragments; peptide and non-peptide mimetics, other analogs, or combinations thereof, E4orf4 mRNA, E4orf6 mRNA, compounds which increase the stability of E4orf4 and/or E4orf6, or any compound which increases the apoptosis-inducing activity of E4orf4 and/or E4orf6.

a) Protein Therapy

To introduce E4orf4 or E4orf 6 proteins and polypeptide fragments thereof to transformed cells, it is necessary to obtain large amounts of pure polypeptide from cultured cell systems which can express the polypeptide. Delivery of the polypeptide to the affected tissues (e.g., cancerous tissues) can then be accomplished using appropriate packaging or administrating systems. Alternatively, small molecule analogs may be used and administered to act as E4 death protein agonists and in this manner produce a desired physiological effect. Methods for finding such analogs are provided herein.

Another therapeutic approach within the invention involves administration of recombinant E4 death protein polypeptides, either directly to the site of a desired apoptosis event (for example, by injection) or systemically (for example, by any conventional recombinant protein administration technique).

b) Gene Therapy

Gene therapy is another potential therapeutic approach in which copies of DNA encoding the E4 death proteins or fragments thereof are introduced into selected tissues to successfully encode for abundant polypeptide product in affected cell types (e.g., cancer cells). The DNA must be delivered to those cells in a form in which it can be taken up and encode for sufficient polypeptide product to provide effective function.

Transducing retroviral vectors can be used for somatic cell gene therapy especially because of their high efficiency of infection and stable integration and expression. The full length DNA encoding E4orf4 and/or E4orf6, or portions thereof, can be cloned into a retroviral vector and driven from its endogenous promoter or from the retroviral long terminal repeat or from a promoter specific for the target cell type of interest (such as neurons). Other viral vectors which can be used include adeno-associated virus, vaccinia virus, bovine papilloma virus, or a herpes virus such as Epstein-Barr Virus.

Gene transfer could also be achieved using non-viral means requiring infection of cancer cells in vitro. This would include calcium phosphate, DEAE dextran, electroporation, and protoplast fusion. Liposomes may also be potentially beneficial for delivery of DNA into a cell. Although these methods are available, many of these are lower efficiency.

Transplantation of DNA encoding the E4 death proteins or polypeptide fragments thereof into the affected cells of a patient can also be useful therapy. In this procedure, DNA encoding one or both of the E4 death proteins is transferred into a cultivatable cell type, either exogenously or endogenously to the patient. These cells are then injected serotologically into the targeted tissue(s).

Retroviral vectors, adenoviral vectors, adenovirus-associated viral vectors, or other viral vectors with the appropriate tropism for cells likely to be involved in diseases involving insufficient apoptosis may be used as a gene transfer delivery system for a therapeutic E4 death protein DNA construct. Numerous vectors useful for this purpose are generally known (Miller, Human Gene Therapy 15–14, 1990; Friedman; Science 244:1275–1281, 1989; Eglitis and Anderson, BioTechniques 6:608–614, 1988; Tolstoshev and Anderson, Curr. Opin. Biotech. 1:55–61, 1990; Sharp, The Lancet 337:1277–1278, 1991; Cornetta et al., Nucl. Acid Res. and Mol. Biol. 36:311–322, 1987; Anderson, Science 226:401–409, 1984; Moen, Blood Cells 17:407–416, 1991; Miller et al., Biotech. 7:980–990, 1989; Le Gal La Salle et al., Science 259:988–990, 1993; and Johnson, Chest 107:77S–83S, 1995). Retroviral vectors are particularly well developed and have been used in clinical settings (Rosenberg et al., N. Engl. J. Med 323:370, 1990; Anderson et al., U.S. Pat. No. 5,399,346). Non-viral approaches may also be employed. For example, E4 death proteins may be introduced into a cell by lipofection (Feigner et al., Proc. Natl. Acad. Sci. USA 84:7413, 1987; Ono et al., Neurosci. Lett. 117:259, 1990; Brigham et al., Am. J. Med. Sci. 298:278, 1989; Staubinger et al., Meth. Enz. 101:512, 1983), asialorosonucoid-polylysine conjugation (Wu et al., J. Biol. Chem. 263:14621, 1988; Wu et al., J. Biol. Chem. 264:16985, 1989); or, less preferably, micro-injection under surgical conditions (Wolff et al., Science 247:1465, 1990).

For any of the methods of application described above, the therapeutic E4 death protein-encoding DNA construct is preferably applied to the site of the desired apoptosis event (for example, by-injection). However, it may also be applied to tissue in the vicinity of the desired apoptosis event or to a blood vessel supplying the cells (e.g., cancerous cells) desired to undergo apoptosis.

In the constructs described, DNA expression can be directed from any suitable promoter (e.g., the human cytomegalovirus (CMV), simian virus 40 (SV40), or met-allothionein promoters), and regulated by any appropriate mammalian regulatory element. For example, if desired, enhancers known to preferentially direct gene expression in neural cells, lymphocytes, or muscle cells may be used to direct expression of E4orf4, E4orf6, or polypeptide fragments thereof. The enhancers used could include, without limitation, those that are characterized as tissue- or cell-specific in their expression. Alternatively, regulation of expression may be mediated by the cognate regulatory sequences or, if desired, by regulatory sequences derived from a heterologous source, including any of the promoters or regulatory elements described above.

E4 death protein gene therapy may also be accomplished by direct administration of E4orf4 or E4orf6 mRNA to a cell that is desired to undergo undesired apoptosis. The mRNA may be produced and isolated by any standard technique, but is most readily produced by in vitro transcription using encoding DNA under the control of a high efficiency promoter (e.g., the T7 promoter). Administration of mRNA to cells can be carried out by any of the methods for direct nucleic acid administration described above.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method inducing apoptosis of a cell, said method comprising (a) administering to said cell by intratumoral injection a nucleic acid encoding a polypeptide comprising the sequence of SEQ ID NO.: 4 and capable of inducing apoptosis, said nucleic acid operably linked to a heterologous regulatory sequence for expression of said polypeptide, and (b) expressing said nucleic acid in said cell, wherein expressing said nucleic acid in said cell induces apoptosis of said cell.

2. The method of claim 1, wherein said regulatory sequence is capable of expressing said nucleic acid in a constitutive, inducible, or cell-type specific manner.

3. The method of claim 1, wherein said nucleic acid is in an adenoviral vector or a retroviral vector.

4. The method of claim 1, wherein said cell is a cancer cell.

5. A pharmaceutical composition comprising (i) an expression vector comprising a nucleic acid encoding an E4orf4 polypeptide comprising the sequence of SEQ ID NO.: 4 and capable of inducing apoptosis, and (ii) a pharmaceutically acceptable carrier, wherein said nucleic acid is operably linked to a heterologous regulatory sequence for expression of said E4orf4 polypeptide in a mammalian cell, and wherein E4 polypeptides other than said E4orf4 polypeptide are not expressed by said vector.

6. The composition of claim 5, wherein said regulatory sequence is capable of expressing said nucleic acid in a constitutive, inducible, or cell-type specific manner.

7. The composition of claim 5, wherein said nucleic acid is in an adenoviral vector or a retroviral vector.

8. An expression vector comprising a nucleic acid encoding an E4orf4 polypeptide comprising the sequence of SEQ ID NO.: 4 and capable of inducing apoptosis, wherein said nucleic acid is operably linked to a heterologous regulatory sequence for expression of said E4orf4 polypeptide in a mammalian cell, and wherein E4 polypeptides other than said E4orf4 polypeptide are not expressed by said vector.

9. The expression vector of claim 8, wherein said regulatory sequence is capable of expressing said nucleic acid in a constitutive, inducible, or cell-type specific manner.

10. The expression vector of claim 8, wherein said expression vector is an adenovirol vector or a retroviral vector.

* * * * *

SEQUENCE LISTING

<160> NUMBER OF SEQ ID NOS: 4

<210> SEQ ID NO 1
<211> LENGTH: 885
<212> TYPE: DNA
<213> ORGANISM: Adenovirus

<400> SEQUENCE: 1

```
atgactacgt ccggcgttcc atttggcatg acactacgac caacacgatc tcggttgtct    60
cggcgcactc cgtacagtag ggatcgtcta cctccttttg agacagaaac ccgcgctacc   120
atactggagg atcatccgct gctgcccgaa tgtaacactt tgacaatgca caacgtgagt   180
tacgtgcgag gtcttccctg cagtgtggga tttacgctga ttcaggaatg ggttgttccc   240
tgggatatgg ttctaacgcg ggaggagctt gtaatcctga ggaagtgtat gcacgtgtgc   300
ctgtgttgtg ccaacattga tatcatgacg agcatgatga tccatggtta cgagtcctgg   360
gctctccact gtcattgttc cagtcccggt tccctgcagt gtatagccgg cgggcaggtt   420
ttggccagct ggtttaggat ggtggtggat ggcgccatgt taatcagag gtttatatgg    480 taccgggagg tggtgaatta caacatgcca aaagaggtaa tgtttatgtc cagcgtgttt   540 atgagggtc gccacttaat ctacctgcgc ttgtggtatg atggccacgt gggttctgtg   600
gtccccgcca tgagctttgg atacagcgcc ttgcactgtg ggattttgaa caatattgtg   660
gtgctgtgct gcagttactg tgctgattta agtgagatca gggtgcgctg ctgtgcccgg   720
aggacaaggc gccttatgct gcgggcggtg cgaatcatcg ctgaggagac cactgccatg   780
ttgtattcct gcaggacgga gcggcggcgg cagcagttta ttcgcgcgct gctgcagcac   840
caccgcccta tcctgatgca cgattatgac tctaccccca tgtag                   885
```

<210> SEQ ID NO 2
<211> LENGTH: 294
<212> TYPE: PRT
<213> ORGANISM: Adenovirus

<400> SEQUENCE: 2

```
Met Thr Thr Ser Gly Val Pro Phe Gly Met Thr Leu Arg Pro Thr Arg
 1               5                  10                  15

Ser Arg Leu Ser Arg Arg Thr Pro Tyr Ser Arg Asp Arg Leu Pro Pro
                20                  25                  30

Phe Glu Thr Glu Thr Arg Ala Thr Ile Leu Glu Asp His Pro Leu Leu
            35                  40                  45

Pro Glu Cys Asn Thr Leu Thr Met His Asn Val Ser Tyr Val Arg Gly
        50                  55                  60

Leu Pro Cys Ser Val Gly Phe Thr Leu Ile Gln Glu Trp Val Val Pro
    65                  70                  75                  80

Trp Asp Met Val Leu Thr Arg Glu Glu Leu Val Ile Leu Arg Lys Cys
                85                  90                  95

Met His Val Cys Leu Cys Cys Ala Asn Ile Asp Ile Met Thr Ser Met
```

```
                 100                 105                 110
Met Ile His Gly Tyr Glu Ser Trp Ala Leu His Cys His Cys Ser Ser
                115                 120                 125
Pro Gly Ser Leu Gln Cys Ile Ala Gly Gly Gln Val Leu Ala Ser Trp
        130                 135                 140
Phe Arg Met Val Val Asp Gly Ala Met Phe Asn Gln Arg Phe Ile Trp
145                 150                 155                 160
Tyr Arg Glu Val Val Asn Tyr Asn Met Pro Lys Glu Val Met Phe Met
                165                 170                 175
Ser Ser Val Phe Met Arg Gly Arg His Leu Ile Tyr Leu Arg Leu Trp
                180                 185                 190
Tyr Asp Gly His Val Gly Ser Val Val Pro Ala Met Ser Phe Gly Tyr
            195                 200                 205
Ser Ala Leu His Cys Gly Ile Leu Asn Asn Ile Val Val Leu Cys Cys
        210                 215                 220
Ser Tyr Cys Ala Asp Leu Ser Glu Ile Arg Val Arg Cys Cys Ala Arg
225                 230                 235                 240
Arg Thr Arg Arg Leu Met Leu Arg Ala Val Arg Ile Ile Ala Glu Glu
                245                 250                 255
Thr Thr Ala Met Leu Tyr Ser Cys Arg Thr Glu Arg Arg Arg Gln Gln
                260                 265                 270
Phe Ile Arg Ala Leu Leu Gln His His Arg Pro Ile Leu Met His Asp
            275                 280                 285
Tyr Asp Ser Thr Pro Met
        290

<210> SEQ ID NO 3
<211> LENGTH: 345
<212> TYPE: DNA
<213> ORGANISM: Adenovirus

<400> SEQUENCE: 3
atggttcttc cagctcttcc cgctcctccc gtgtgtgact cgcagaacga atgtgtaggt     60
tggctgggtg tggcttattc tgcggtggtg gatgttatca gggcagcggc gcatgaagga    120
gtttacatag aacccgaagc caggggggcgc ctggatgctt tgagagagtg gatatactac    180
aactactaca cagagcgatc taagcggcga gaccggagac gcagatctgt tgtcacgcc     240 cgcacctggt tttgcttcag gaaatatgac tacgtccggc gttccatttg gcatgacact    300
acgaccaaca cgatctcggt tgtctcggcg cactccgtac agtag                    345

<210> SEQ ID NO 4
<211> LENGTH: 114
<212> TYPE: PRT
<213> ORGANISM: Adenovirus

<400> SEQUENCE: 4

Met Val Leu Pro Ala Leu Pro Ala Pro Pro Val Cys Asp Ser Gln Asn
1               5                   10                  15
Glu Cys Val Gly Trp Leu Gly Val Ala Tyr Ser Ala Val Val Asp Val
                20                  25                  30
Ile Arg Ala Ala Ala His Glu Gly Val Tyr Ile Glu Pro Glu Ala Arg
            35                  40                  45
Gly Arg Leu Asp Ala Leu Arg Glu Trp Ile Tyr Tyr Asn Tyr Tyr Thr
        50                  55                  60
Glu Arg Ser Lys Arg Arg Asp Arg Arg Arg Ser Val Cys His Ala
```

-continued

```
          65                  70                  75                  80
Arg Thr Trp Phe Cys Phe Arg Lys Tyr Asp Tyr Val Arg Arg Ser Ile
                85                  90                  95

Trp His Asp Thr Thr Thr Asn Thr Ile Ser Val Val Ser Ala His Ser
                100                 105                 110

Val Gln
```